(12) United States Patent
Skorich et al.

(10) Patent No.: US 11,628,007 B2
(45) Date of Patent: Apr. 18, 2023

(54) CRYOPROBE

(71) Applicant: AtriCure, Inc., Mason, OH (US)

(72) Inventors: Stefan Skorich, Minneapolis, MN (US); David Wilson, Mason, OH (US); Todd Frangolis, Mason, OH (US); Christopher Widenhouse, Mason, OH (US); Frank Fago, Mason, OH (US)

(73) Assignee: AtriCure, Inc., Mason, OH (US)

( * ) Notice: Subject to any disclaimer, the term of this patent is extended or adjusted under 35 U.S.C. 154(b) by 394 days.

(21) Appl. No.: 16/569,777

(22) Filed: Sep. 13, 2019

(65) Prior Publication Data

US 2020/0085485 A1 Mar. 19, 2020

Related U.S. Application Data

(60) Provisional application No. 62/731,310, filed on Sep. 14, 2018.

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/00577* (2013.01);
(Continued)

(58) Field of Classification Search
CPC .......... A61B 18/02; A61B 2018/00041; A61B 2018/00434; A61B 2018/00577;
(Continued)

(56) References Cited

U.S. PATENT DOCUMENTS 3,630,203 A * 12/1971 Sellinger ............ A61B 18/0218
606/24
3,807,403 A * 4/1974 Stumpf .................... A61F 7/12
606/26
(Continued)

FOREIGN PATENT DOCUMENTS

EP 0741546 11/1996
JP S51-121993 10/1976
(Continued)

OTHER PUBLICATIONS

Atricure, Inc., The CryoICE® cryo ablation probe is now available for cryoanalgesia therapy, Press Release, Business Wire, West Chester, Ohio, Mar. 18, 2015.
(Continued)

*Primary Examiner* — Daniel W Fowler
(74) *Attorney, Agent, or Firm* — Dorton & Willis, LLP; Ryan Willis

(57) ABSTRACT

Cryosurgical devices, such as cryosurgical probes (cryoprobes) are disclosed. Some example embodiments may include an elongated shaft at least partially housing or delineating a fluid supply conduit and a fluid exhaust conduit, the elongated shaft including a distal ablation section terminating at a closed distal end, a housing at least partially circumscribing at least a portion of a proximal end of the elongated shaft and receiving or delineating at least a portion of the fluid supply conduit and a portion of the fluid exhaust conduit; and/or a flow restricting element in fluid communication with the fluid exhaust conduit, the flow restricting element regulating the flow of fluid through at least a portion of the fluid exhaust conduit.

33 Claims, 17 Drawing Sheets

(52) U.S. Cl.
CPC ............... *A61B 2018/00744* (2013.01); *A61B 2018/0268* (2013.01); *A61B 2560/04* (2013.01)

(58) Field of Classification Search
CPC ........... A61B 2018/00744; A61B 2018/00821; A61B 2018/0268
See application file for complete search history.

(56) References Cited

U.S. PATENT DOCUMENTS

| | | | | |
|---|---|---|---|---|
| 3,971,383 | A | * 7/1976 | van Gerven | A61B 18/02 606/23 |
| 4,206,760 | A | * 6/1980 | Davis | A61B 18/02 606/23 |
| 4,236,518 | A | * 12/1980 | Floyd | A61B 18/02 137/614.14 |
| 4,278,090 | A | 7/1981 | van Gerven | |
| 5,078,713 | A | * 1/1992 | Varney | A61B 18/02 606/22 |
| 5,324,286 | A | * 6/1994 | Fowle | A61B 18/02 606/23 |
| 5,400,602 | A | * 3/1995 | Chang | A61B 18/02 128/DIG. 27 |
| 5,423,807 | A | 6/1995 | Milder | |
| 5,992,158 | A | 11/1999 | Goddard et al. | |
| 6,039,730 | A | * 3/2000 | Rabin | A61B 18/02 606/21 |
| 6,149,677 | A | * 11/2000 | Dobak, III | A61F 7/12 607/104 |
| 6,161,543 | A | 12/2000 | Cox et al. | |
| 6,270,493 | B1 | * 8/2001 | Lalonde | A61B 18/02 606/23 |
| 6,379,348 | B1 | 4/2002 | Onik | |
| 8,740,891 | B2 | 6/2014 | Babkin et al. | |
| 9,381,114 | B2 | 7/2016 | Underwood et al. | |
| 2003/0060815 | A1 | * 3/2003 | Lalonde | A61B 18/02 606/23 |
| 2004/0034365 | A1 | * 2/2004 | Lentz | A61B 18/02 606/108 |
| 2006/0084962 | A1 | * 4/2006 | Joye | A61B 18/02 606/21 |
| 2008/0027422 | A1 | * 1/2008 | Vancelette | A61B 18/02 606/23 |
| 2011/0264086 | A1 | 10/2011 | Ingle | |
| 2012/0089136 | A1 | 4/2012 | Levin et al. | |
| 2012/0089211 | A1 | 4/2012 | Curtis et al. | |
| 2015/0148791 | A1 | * 5/2015 | Birdsall | A61B 18/02 606/22 |
| 2017/0021132 | A1 | 1/2017 | Barrish | |

FOREIGN PATENT DOCUMENTS

| | | |
|---|---|---|
| JP | H09-511414 | 11/1997 |
| JP | 2012-523296 | 10/2012 |
| JP | 2013-544135 | 12/2013 |
| WO | 95/19738 | 7/1995 |
| WO | 2008142686 A2 | 11/2008 |
| WO | 2011119279 | 9/2011 |
| WO | 2012/058430 | 5/2012 |
| WO | 2014189601 A1 | 11/2014 |
| WO | PCT/US2019/050941 | 1/2020 |

OTHER PUBLICATIONS

Atricure, Inc., Frost will evaluate cryoablation of peripheral nerves for the temporary management of post-operative pain, Press Release, Business Wire, Mason, Ohio, Jun. 21, 2016.
European Patent Office, extended European search report in EP 19861001, dated Jan. 4, 2022.
Japan Patent Office, office action in JP 2021-512504, dated Jun. 27, 2022.

* cited by examiner

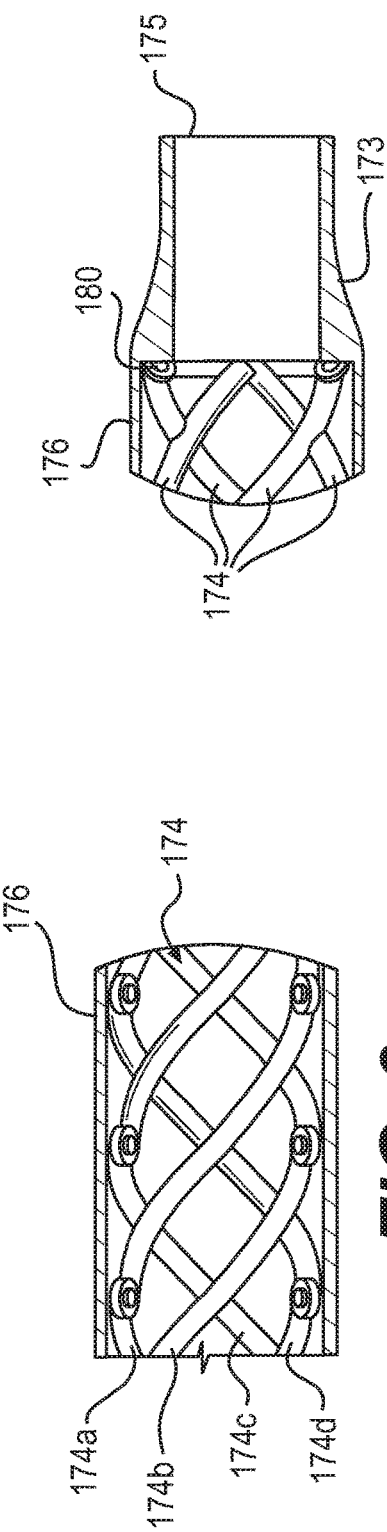
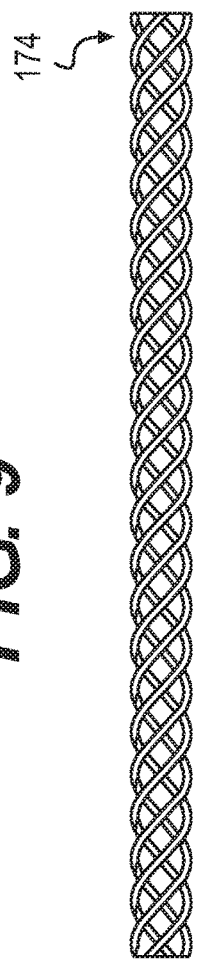

CRYOPROBE

CROSS REFERENCE TO RELATED APPLICATIONS

This application claims the benefit of U.S. Provisional Application No. 62/731,310, filed Sep. 14, 2018, which is incorporated by reference.

INTRODUCTION TO THE INVENTION

The present disclosure is directed to cryoprobes and, more specifically, to cryoprobes having malleable shafts interconnecting an ablation tip and a handle control.

The present disclosure contemplates that the temperature of an ablation tip of a cryoprobe may be related to the boiling temperature (e.g., vaporization temperature) of the cryogen, which may be related to the cryogen pressure at the ablation tip. The present disclosure contemplates that, for example, the cryogen pressure at the ablation tip may vary substantially, thus affecting the temperature of the ablation tip, in cryoprobes in which the back pressure in the cryogen exhaust stream varies. The present disclosure provides methods and apparatus that improve regulation of the cryogen exhaust stream back pressure. Additionally, the present disclosure contemplates that the cryogen pressure at the ablation tip may be affected by the characteristics of the flowpath leading to the ablation tip. The present disclosure provides methods and apparatus that improve the supply of cryogen to the ablation tip to achieve desired temperatures. In this manner, the present disclosure provides improvements over the prior art related to regulation of the temperature at the ablation tip of a cryoprobe.

The present disclosure contemplates that while cryoprobes may utilize extremely cold temperatures to achieve desired effects at desired locations, exposure of other locations to extremely cold temperatures may cause undesired effects. The present disclosure contemplates that, for example, it may be desirable for the ablation tip of a cryoprobe to be extremely cold while the shaft on which the tip is disposed remains above a tissue-ablating temperature. The present disclosure provides methods and apparatus that improve the ability of cryoprobes to cool an ablation tip to a desired temperature while maintaining other external portions of the cryoprobe at warmer temperatures. In this manner, the present disclosure provides improvements over the prior art related to cryoprobes.

The present disclosure contemplates that the rate of heat transfer and/or the extent of ablation may depend upon the manner in which a cryoprobe engages the target tissue. For example, the present disclosure contemplates that the configuration of a cryoprobe may affect the difficulty of accessing, engaging, and ablating a particular tissue to a desired extent. The present disclosure provides methods and apparatus involving cryoprobe configurations adapted to achieve desired tissue ablation, such as cryoanalgesia of intercostal nerves. In this manner, the present disclosure provides improvements of the prior art related to cryoprobes, which may be used for cryoanalgesia, for example.

It is a first aspect of the present disclosure to provide a cryogenic probe including an elongated shaft at least partially housing or delineating a fluid supply conduit and a fluid exhaust conduit, the elongated shaft including a distal ablation section terminating at a closed distal end; a housing at least partially circumscribing at least a portion of a proximal end of the elongated shaft and receiving or delineating at least a portion of the fluid supply conduit and a portion of the fluid exhaust conduit; and/or a flow restricting element in fluid communication with the fluid exhaust conduit, the flow restricting element regulating the flow of fluid through at least a portion of the fluid exhaust conduit.

In an embodiment, the flow restricting element may include a constriction fluidicly interposing the fluid exhaust conduit and an exhaust line. The cross-sectional area for fluid flow of the constriction may be less than about 70% of a cross-sectional area for fluid flow of the exhaust line. The cross-sectional area for fluid flow of the constriction may be less than about 50% of a cross-sectional area for fluid flow of the exhaust line. The cross-sectional area for fluid flow of the constriction may be less than about 30% of a cross-sectional area for fluid flow of the exhaust line. The cross-sectional area for fluid flow of the constriction may be less than about 15% of a cross-sectional area for fluid flow of the exhaust line. The cross-sectional area for fluid flow of the constriction may be about 10% of a cross-sectional area for fluid flow of the exhaust line.

In an embodiment, the flow restricting element may include a pressure valve in fluid communication with the fluid supply conduit and the fluid exhaust conduit, the pressure valve regulating the flow of fluid through at least a portion of the fluid exhaust conduit. The pressure valve may include a valve plug configured to engage a valve seat and form a seal therebetween. The valve plug may be biased to engage the valve seat. The valve plug may be spring biased to engage the valve seat and at least a portion of the spring may be located within the distal ablation section.

In an embodiment, the distal ablation section may include a bulbous exterior surface. The bulbous exterior surface may include a semispherical portion. The distal ablation section may include a necked down section to vary a cross-section of the distal ablation section. At least a portion of the fluid supply conduit may extend into the distal ablation section. At least the portion of the fluid supply conduit extending into the distal ablation section may include a fluid flow constriction prior to reaching a nozzle within the distal ablation section. A proximal aspect of the distal ablation section may be fluidically sealed to a distal aspect of the elongated shaft using at least one of an adhesive bond and a weld.

In an embodiment, the cryogenic probe may include a flexible insulated conduit circumscribing the elongated shaft along at least a portion of its longitudinal length. The flexible insulated conduit may circumscribe the elongated shaft along a majority of its longitudinal length. The flexible insulated conduit may include a spacer interposing an outer cover of the flexible insulated conduit and an exterior of the elongated shaft. The spacer may include a foam, a helix, and/or a plurality of polymer helices. The polymer helices may be longitudinally offset from one another along the flexible insulated conduit and/or each of the polymer helices may have a common axial dimension. The spacer may terminate before reaching at least one of a proximal end and a distal end of the flexible insulated conduit. The flexible insulated conduit may be necked down to have an outside dominant dimension less than an outer diameter of the helix at at least one of a proximal end and a distal end of the flexible insulated conduit.

In an embodiment, the elongated shaft may provide greater than 180 degrees of bending without fracturing. An interior of the elongated shaft and an exterior of the fluid supply line may delineate the fluid exhaust line. An interior of the elongated shaft and an exterior of the fluid exhaust line may delineate the fluid supply line.

In an embodiment, the bulbous exterior surface may extend longitudinally more than half of a longitudinal length of an exposed exterior surface of the distal ablation section. The bulbous exterior surface may extend longitudinally less than half of a longitudinal length of an exposed exterior surface of the distal ablation section.

In an embodiment, the distal ablation section may be configured to withstand a pressure during a warming operation which includes blocking the flow of the fluid through the fluid exhaust conduit. The housing may include an interior cavity housing an adapter operative to change coaxial orientation of the fluid supply conduit and the fluid exhaust conduit to parallel orientation.

It is a second aspect of the present disclosure to provide a cryogenic probe including an elongated tube at least partially housing or delineating a fluid supply conduit and a fluid exhaust conduit, the elongated tube including a distal ablation section terminating at a closed distal end, the elongated tube including at least one stagnant fluid pocket interposing an exterior of the conduit and at least one of the fluid supply conduit and the fluid exhaust conduit; and/or a housing at least partially circumscribing at least a portion of a proximal end of the elongated tube and receiving or delineating at least a portion of the fluid supply conduit and a portion of the fluid exhaust conduit.

In an embodiment, the stagnant fluid pocket may be at least partially delineated by a spacer helix. The spacer helix may include a plurality of spacer helices. The plurality of spacer helices may be longitudinally offset from one another along a length of the conduit. The spacer helix may include an insulative material.

In an embodiment, the at least one stagnant fluid pocket may be at least partially delineated by an insert that also provides a passageway for at least one of the fluid supply conduit and the fluid exhaust conduit. The insert may include a triangular cross-section and/or may include separate passageways for the fluid supply conduit and the fluid exhaust conduit. The separate passageways for the fluid supply conduit and the fluid exhaust conduit may include at least one of a plurality of fluid supply conduits and a plurality of fluid exhaust conduits. The insert may include a geometric shaped cross-section and/or may include separate conduits for the fluid supply conduit and the fluid exhaust conduit, the geometric shaped cross-section having four or more sides. The separate conduits for the fluid supply conduit and the fluid exhaust conduit may include at least one of a plurality of fluid supply conduits and a plurality of fluid exhaust conduits.

It is a third aspect of the present disclosure to provide a cryogenic probe including an elongated tube including an insulating section at least partially housing or delineating a fluid supply conduit and a fluid exhaust conduit, the elongated tube including a distal ablation section terminating at a closed distal end, the fluid supply conduit terminating proximate the closed distal end and within the distal ablation section, the fluid supply conduit having a cross-section at termination substantially less than a cross-section upstream from termination; and/or a housing at least partially circumscribing at least a portion of a proximal end of the elongated tube and receiving or delineating at least a portion of the fluid supply conduit and a portion of the fluid exhaust conduit.

In an embodiment, the cross-section of the fluid supply conduit at termination may be defined by at least one of a fluid flow feature and a nozzle, the at least one of the fluid flow feature and the nozzle having a cross-section that is substantially less than the cross-section of the fluid supply conduit upstream from termination.

It is a fourth aspect of the present disclosure to provide a method of providing cryoanalgesia, the method including positioning a bulbous distal exterior surface of an ablation tip of a cryogenic probe proximate a target nerve, the target nerve comprising axons and surrounding tubular structures; disrupting the axons of the target nerve while leaving at least some of the surrounding tubular structures intact by delivering cryogenic fluid to the cryogenic probe to cool the ablation tip; warming the cryogenic probe; and/or removing the bulbous distal exterior surface from proximate the target nerve.

In an embodiment, positioning the bulbous distal exterior surface of the ablation tip of the cryogenic probe proximate the target nerve may include placing the bulbous distal exterior surface of the ablation tip in direct contact with the target nerve. Positioning the bulbous distal exterior surface of the ablation tip of the cryogenic probe proximate the target nerve may include placing the bulbous distal exterior surface of the ablation tip in proximity to the target nerve but not in direct contact with the target nerve. Warming the cryogenic probe may include blocking flow of exhausted cryogenic fluid coming from the cryogenic probe while continuing to supply cryogenic fluid to the cryogenic probe. The ablation tip may include ablation tip proximal exterior surface with a substantially constant axial profile, the diameter of which is less than a diameter of the bulbous distal exterior surface. The bulbous exterior surface may include a semi-spherical surface having a diameter between approximately 3.0 and approximately 18.0 millimeters. The method may include repeating the positioning, disrupting, warming, and removing operations on a second target nerve. The target nerve may include an intercostal nerve. The method may include, before positioning the bulbous distal exterior surface of the ablation tip of the cryogenic probe proximate the target nerve, bending the cryogenic probe. Disrupting the axons of the target nerve while leaving at least some of the surrounding tubular structures intact may include leaving at least one of an endoneurium, a perineurium, a fascicle, and an epineurium intact. Disrupting the axons of the target nerve while leaving at least some of the surrounding tubular structures intact may include an endoneurium and a perineurium intact.

BRIEF DESCRIPTION OF THE DRAWINGS

FIG. 8 is a profile view of a first exemplary insulated conduit in accordance with the instant disclosure.

FIG. 9 is a longitudinal cross-sectional view of the first exemplary insulated conduit along a majority of the insulated conduit's length.

FIG. 10 is a longitudinal cross-sectional view of the first exemplary insulated conduit at its proximal end.

FIG. 11 is a profile view of a first exemplary spacer in accordance with the instant disclosure.

DETAILED DESCRIPTION

The exemplary embodiments of the present disclosure are described and illustrated below to encompass exemplary cryogenic probes, methods of fabricating cryogenic probes, and methods of using cryogenic probes as part of pain management procedures. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
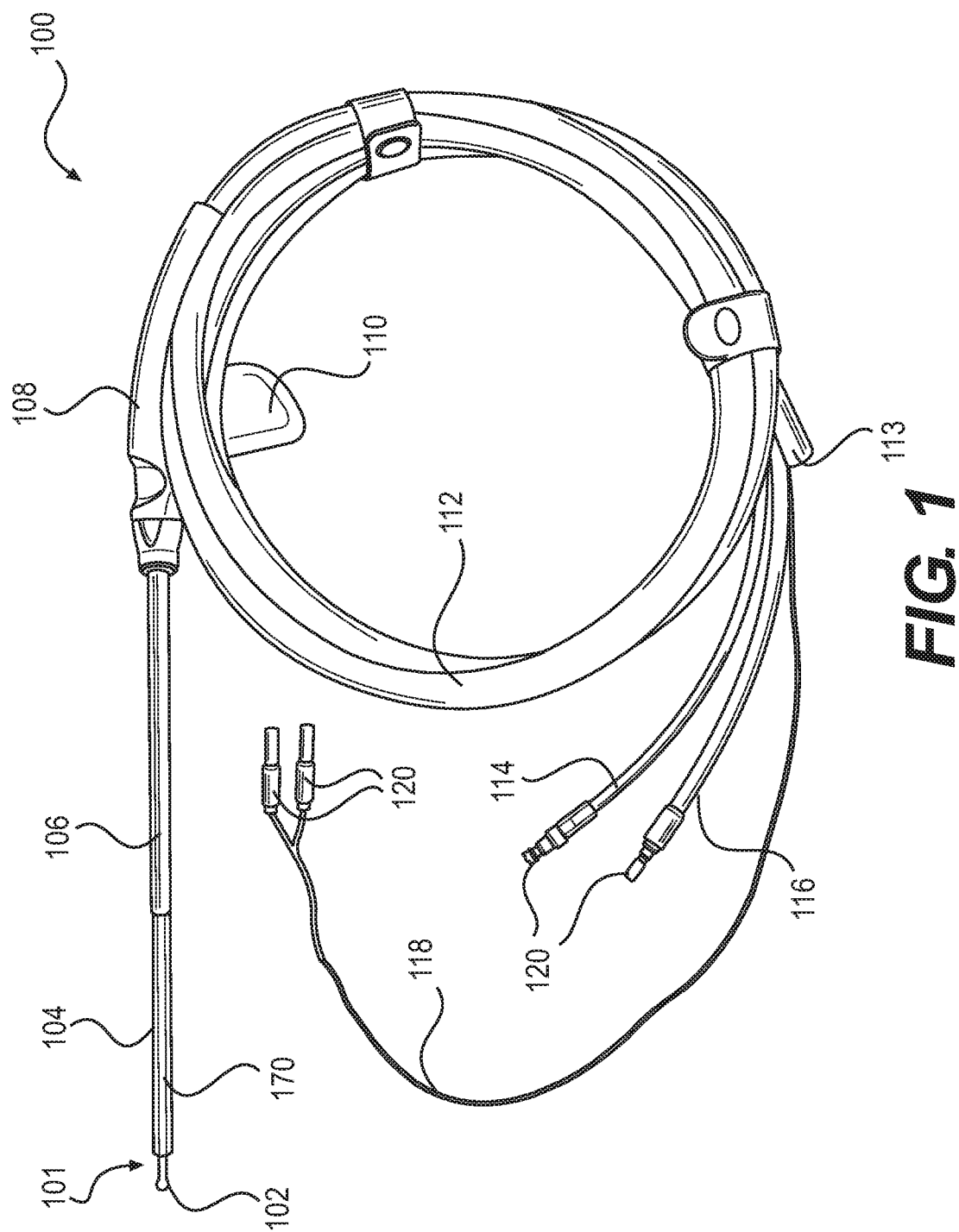
FIG. 1 is a profile view of a first exemplary cryoprobe in accordance with the instant disclosure.
Figure 2:
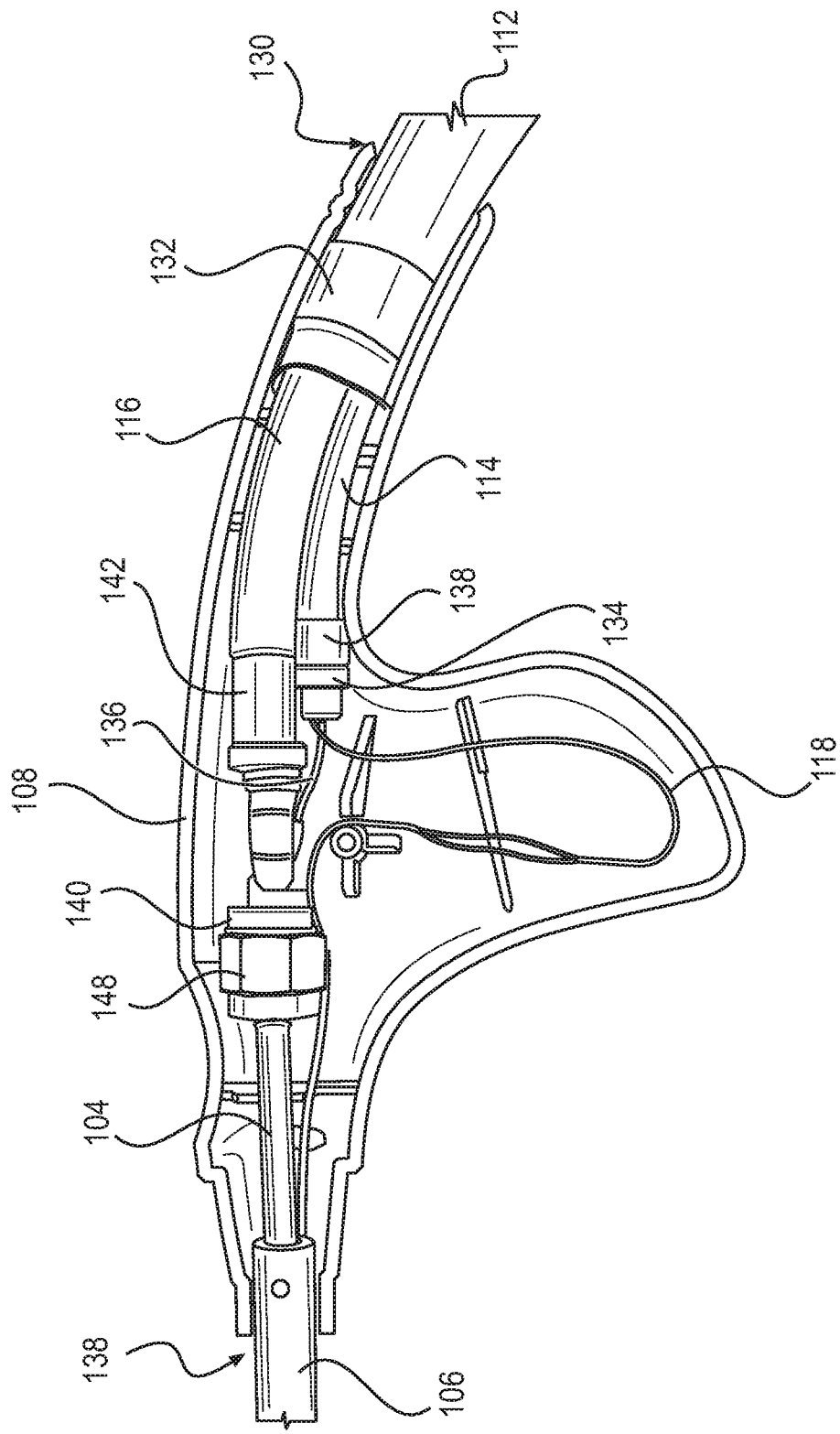
FIG. 2 is a profile view with one half of the handle housing removed to show internal components within the handle housing of the first exemplary cryoprobe of FIG. 1.
Figure 3:
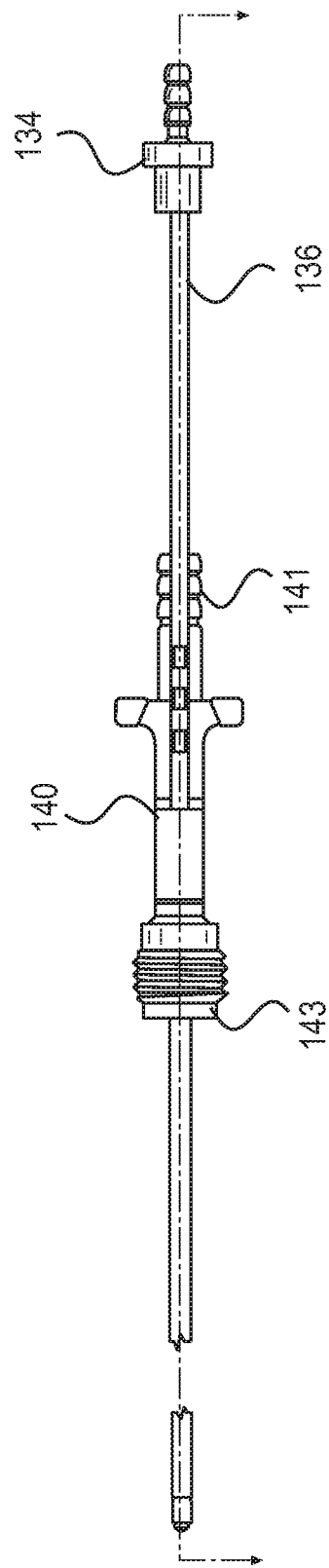
FIG. 3 is an overhead view of adapters and a hypotube of the first exemplary cryoprobe of FIG. 1.

Referencing FIG. 1, a first exemplary cryogenic probe (cryoprobe) 100 may comprise a distal ablation section 101 including an ablation tip 102 connected to a flexible or malleable elongated shaft 104 extending through an insulated tube 106 and into a handle housing 108. By way of example, a distance between the ablation tip 102 and the handle housing 108 may vary depending upon intended application but, in exemplary form, may range between approximately four to thirty inches. In exemplary form, the insulated tube 106 may be substantially rigid and fixedly mounted to the handle housing 108 in order to shield portions of the malleable shaft 104 from direct contact with its immediate surroundings (including adjacent tissue when inserted into a mammalian body). In this exemplary embodiment, the handle housing 108 may include a pistol grip 110 and an internal cavity extending therethrough that accommodates connections between the malleable shaft 104 and a connection bundle 112. In addition to the pistol grip 110, other methods known in the art to grip may be used.

The connection bundle 112 may, in exemplary form, comprise a braided sleeve 113 that circumscribes a supply line 114 directing a working fluid from a fluid source (not shown) to inside the handle housing 108, as well as an exhaust line 116 directing the working fluid from within the handle housing to a collection location (not shown) such as, without limitation, a fluid recycling tank. In addition to the exemplary braided sleeve 113, other thicknesses and configurations of the braided sleeve may be used to cover the supply line 114. Exemplary braided sleeves that may be used as part of the instant disclosure include, without limitation, polyethylene terephthalate (PET) braided monofilament yarns such as those available from TechFlex of Sparta, N.J. Moreover, exemplary supply and exhaust lines 114, 116 that may be used as part of the instant disclosure include, without limitation, microbore high pressure hoses such as those available from Hydrotechnik, United Kingdom. In addition to supply and exhaust lines 114, 116, the braided sleeve 113 may also circumscribe one or more thermocouple leads 118 that, in exemplary form, are in electrical communication with one or more thermocouples positioned within or adjacent to at least one of the ablation tip 102 and the malleable shaft 104. Moreover, exemplary thermocouple leads 118 that may be used as part of the instant disclosure include, without limitation, 24 AWG thermocouple wire available from Physitemp, Clifton, N.J. In this exemplary embodiment, the supply and exhaust lines 114, 116 and thermocouple leads 118 may be fitted with quick connect adapters 120 to render the cryoprobe 100 modular. In this fashion, the cryoprobe 100 may be rendered disposable and configured to interface with multiple or repeated use components such as, without limitation, cryogenic fluid tanks, cryogenic fluid recyclers, and medical equipment operative to display temperature readings.

Referring to FIGS. 2-5, the connection bundle 112 may, in exemplary form, extend into a proximal opening 130 of the handle housing 108 and terminate. In this exemplary embodiment, the handle housing 108 may comprise right and left housing sections that, when connected together, define an interior cavity and corresponding proximal and distal openings 130, 138. At the distal termination of the connection bundle 112, a band 132 may circumscribe the connection bundle end as well as the supply and exhaust lines 114, 116 and thermocouple leads 118. In exemplary form, a distal end of the supply line 114 may be fluidically coupled, via a fluid tight seal, to a fluid supply conduit such as a supply hypotube 136 using an adapter 134. By way of example, the adapter 134 may include a ribbed male proximal end that is received within the distal end of the supply line 114, while a female distal end of the adapter receives the supply hypotube 136. In exemplary form, the connection between the supply adapter 134 and the supply line 114 may be supplemented using a crimp ring 138 that circumscribes both the adapter and the supply hypotube to maintain a compression fit between the adapter and supply line. Moreover, the connection between the supply adapter 134 and the supply hypotube 136 may be fluid tight and accomplished using a welding or a brazing process to seat the hypotube within the adapter. In this exemplary embodiment, the supply line 114 may be flexible or malleable and may be fabricated from a single or multilayer construction of various metals and polymers that include, without limitation, aluminum, copper, stainless steel, and thermoplastics (including extruded thermoplastics). By way of further example, the supply line may comprise an inner layer for chemical compatibility (e.g., an extruded polymeric tube) and one or more outer layers for strength (e.g., braided yarn and stainless steel), flexibility abrasion resistance, and/or appearance. And the hypotube 136 and supply adapter 134 may generally be more rigid than the supply line 114 and may be fabricated from stainless steel and have a single or multilayer construction. By way of further example, the hypotube 136 and supply adapter 134 may be fabricated from a single or multilayer construction of various metals and polymers that include, without limitation, aluminum, copper, stainless steel, and thermoplastics (including extruded thermoplastics). Moreover, the hypotube 136 and supply adapter 134 may comprise an inner layer for chemical compatibility (e.g., an extruded polymeric tube) and one or more outer layers for strength (e.g., aluminum, stainless steel, braided yarn), flexibility abrasion resistance, and/or appearance.

Figure 4:
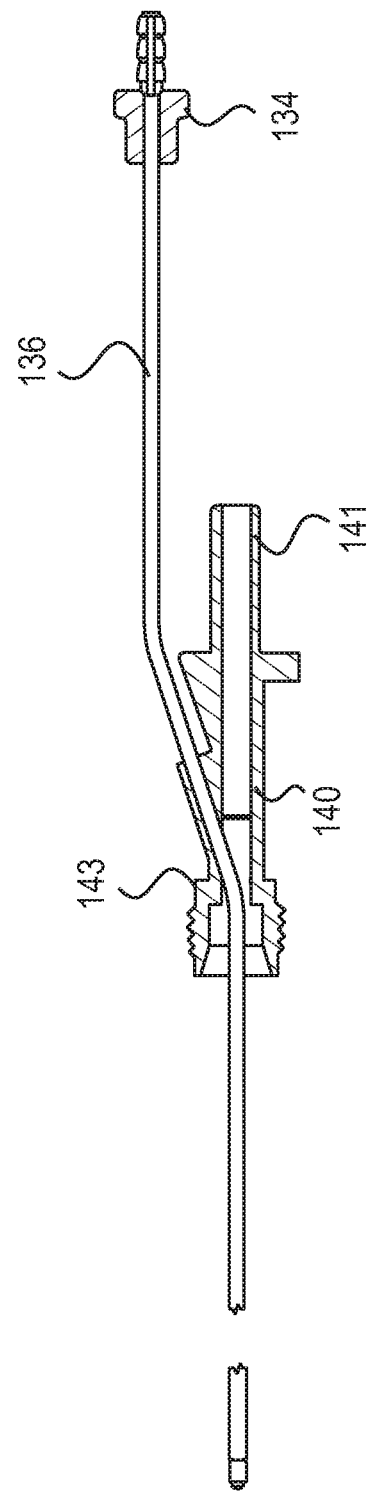
FIG. 4 is a cross-sectional view of FIG. 3 taken along the dominant dimension, longitudinal length.
Figure 5:
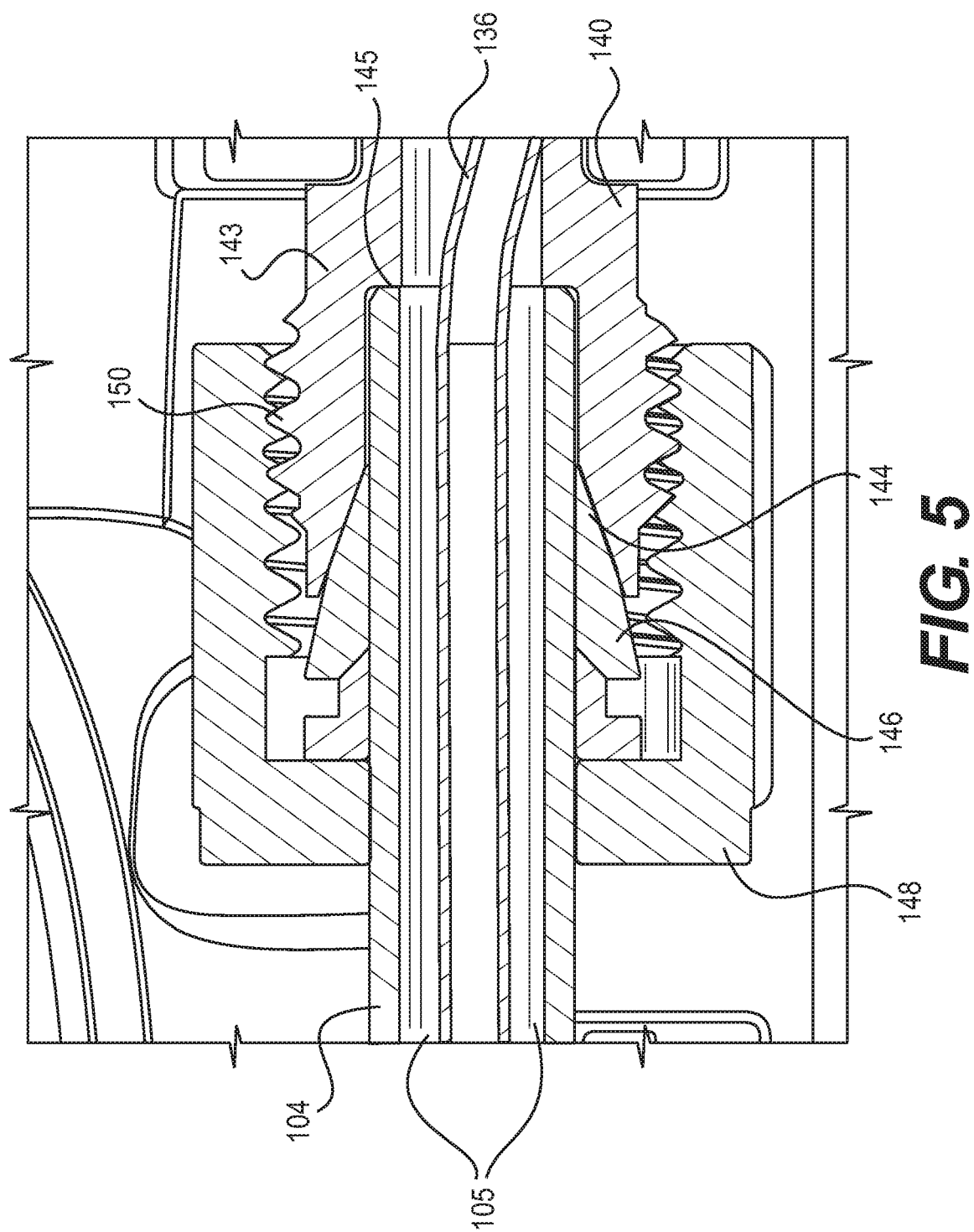
FIG. 5 is a cross-sectional view of an exemplary adapter and related components depicted in FIG. 2.

In exemplary form, the annular space between the exterior of the hypotube 136 and the interior of the malleable shaft 104 may form a fluid exhaust conduit 105, which may convey the exhaust stream from the ablation tip 102 to the exhaust line 116. A distal end of the exhaust line 116 may be fluidically coupled, via a fluid tight seal, to an exhaust adapter 140. Generally, in some exemplary embodiments, the exhaust adapter 140 may be operative to change the arrangement of the fluid exhaust conduit 105 and the fluid supply conduit 136 from a coaxial orientation to a parallel (non-coaxial) orientation. By way of example, the exhaust adapter 140 may include a ribbed male proximal end 141 that is received within the distal end of the exhaust line 116, while a female distal end 143 of the adapter receives a proximal end of the malleable shaft 104. FIG. 4 shows an exemplary adapter 140 having substantially constant cross-sectional area for flow of the exhaust stream between the inlet and outlet ends. But, it should be noted that the cross-sectional area available for flow of the exhaust stream may vary between the inlet and outlet ends as a means to manage back pressure (see FIG. 20). In exemplary form, the connection between the exhaust adapter 140 and the exhaust line 116 may be supplemented using a crimp ring 142 that circumscribes both the adapter and the exhaust line 116 to maintain a compression fit between the adapter and exhaust line. Moreover, the connection between the adapter 140 and the malleable shaft 104 may be fluid tight and accomplished using a brazing process to seat the shaft within the adapter so that the proximal end of the malleable shaft abuts a distal shoulder 145 of the adapter to form a seal therebetween. To help facilitate a continued fluid tight seal between the malleable shaft 104 and the adapter 140, a distal end of the adapter includes a frustoconical taper 144 that receives a frustoconical compression fitting 146 (e.g., a ferrule). The compression fitting 146 is repositioned proximally using a nut 148 threadably engaging helical threads 150 located around the outer periphery of the distal end of the adapter 140. In this manner, as the nut 148 is tightened, the nut pushes against the compression fitting 146, which causes the compression fitting to decrease its outer circumference and tightly grip the exterior of the malleable shaft 104. Continued tightening of the nut 148 exerts even more of a tighter grip between the compression fitting 146 and the exterior of the malleable shaft 104 to inhibit relative movement therebetween. Thread locking agent (not shown) may be applied between the threads of the nut 148 and those of the adapter 140 to inhibit relative movement between the nut and adapter, thus collectively working to maintain the relative position of the malleable shaft 104 in a fluid tight seal against the distal shoulder 145 of the adapter 140. In exemplary form, the adapter 140 includes a passage accommodating throughput of the hypotube 136 so that the distal end of the adapter aligns the hypotube and malleable shaft 104 in a concentric arrangement. In this exemplary embodiment, the exhaust line 116 may be flexible or malleable and may be fabricated from a single or multilayer construction of various metals and polymers that include, without limitation, aluminum, copper, stainless steel, and thermoplastics (including extruded thermoplastics). By way of further example, the exhaust line may comprise an inner layer for chemical compatibility (e.g., an extruded polymeric tube) and one or more outer layers for strength (e.g., braided yarn and stainless steel), flexibility abrasion resistance, and/or appearance. And the malleable shaft 104 and adapter 140 may generally be more rigid than the exhaust line 116 and may be fabricated from stainless steel and have a single or multilayer construction. By way of further example, the malleable shaft 104 and adapter 140 may be fabricated from a single or multilayer construction of various metals and polymers that include, without limitation, aluminum, copper, stainless steel, and thermoplastics (including extruded thermoplastics). Moreover, the malleable shaft 104 and adapter 140 may comprise an inner layer for chemical compatibility (e.g., an extruded polymeric tube) and one or more outer layers for strength (e.g., copper, aluminum, stainless steel, braided yarn), flexibility abrasion resistance, and/or appearance.

Figure 6:
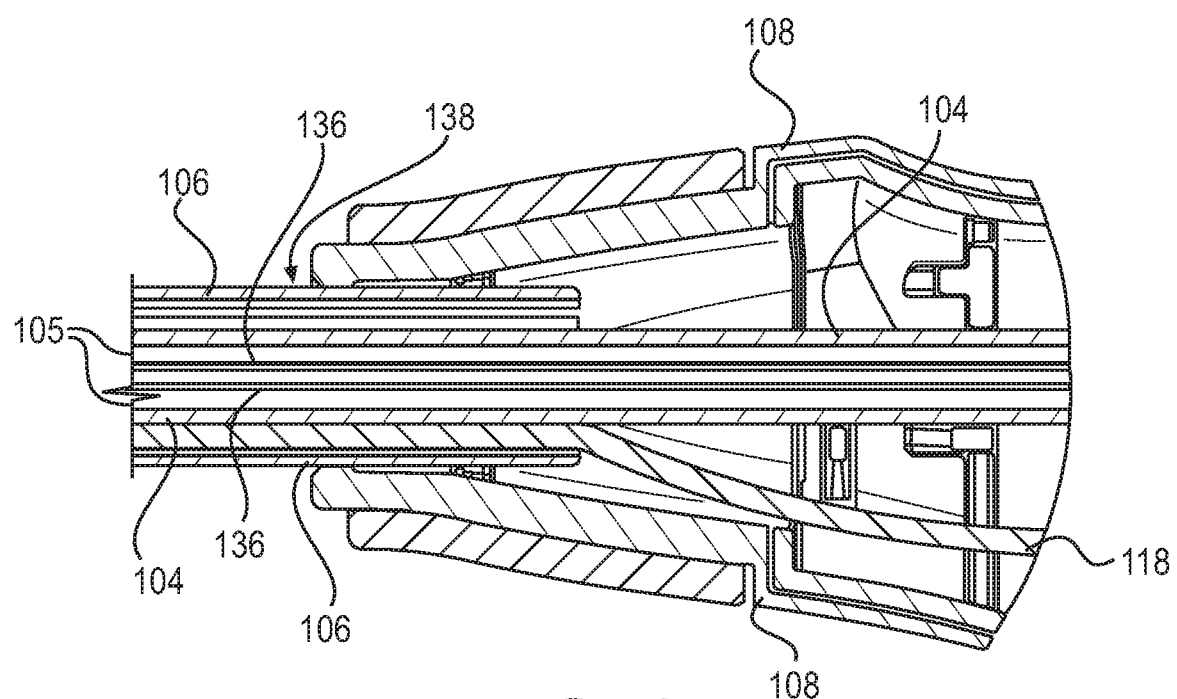
FIG. 6 is a longitudinal cross-sectional view of the first exemplary cryoprobe of FIG. 1 taken at a distal opening of the handle housing.

Referencing FIG. 6, a distal end of the handle housing 108 defines the distal opening 138 through which may extend the hypotube 136, malleable shaft 104, thermocouple leads 118, and insulated tube 106. By way of further example, the hypotube 136 may be concentrically located within the malleable shaft 104, while the thermocouple leads 118 run along an exterior of the malleable shaft. In addition, the insulated tube 106 may be compression fit over the malleable shaft 104 and the thermocouple leads 118.

Figure 7:
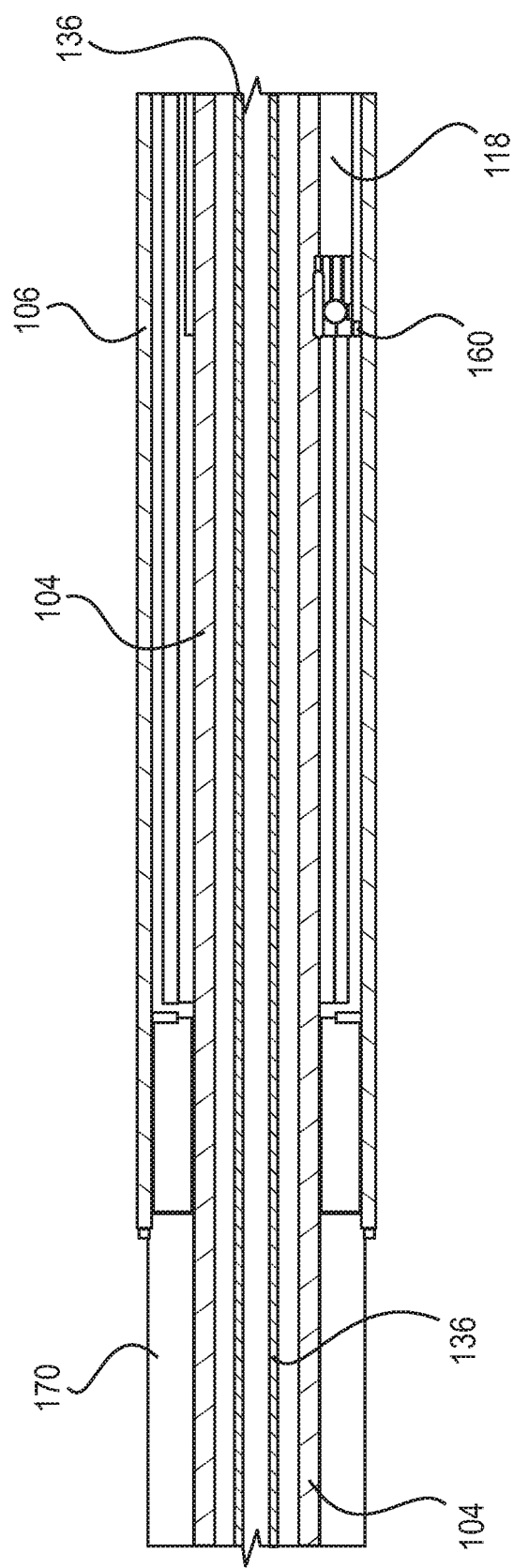
FIG. 7 is a longitudinal cross-sectional view of the first exemplary cryoprobe of FIG. 1 taken along a transition length between the insulated tube and insulated conduit.
Figure 12:
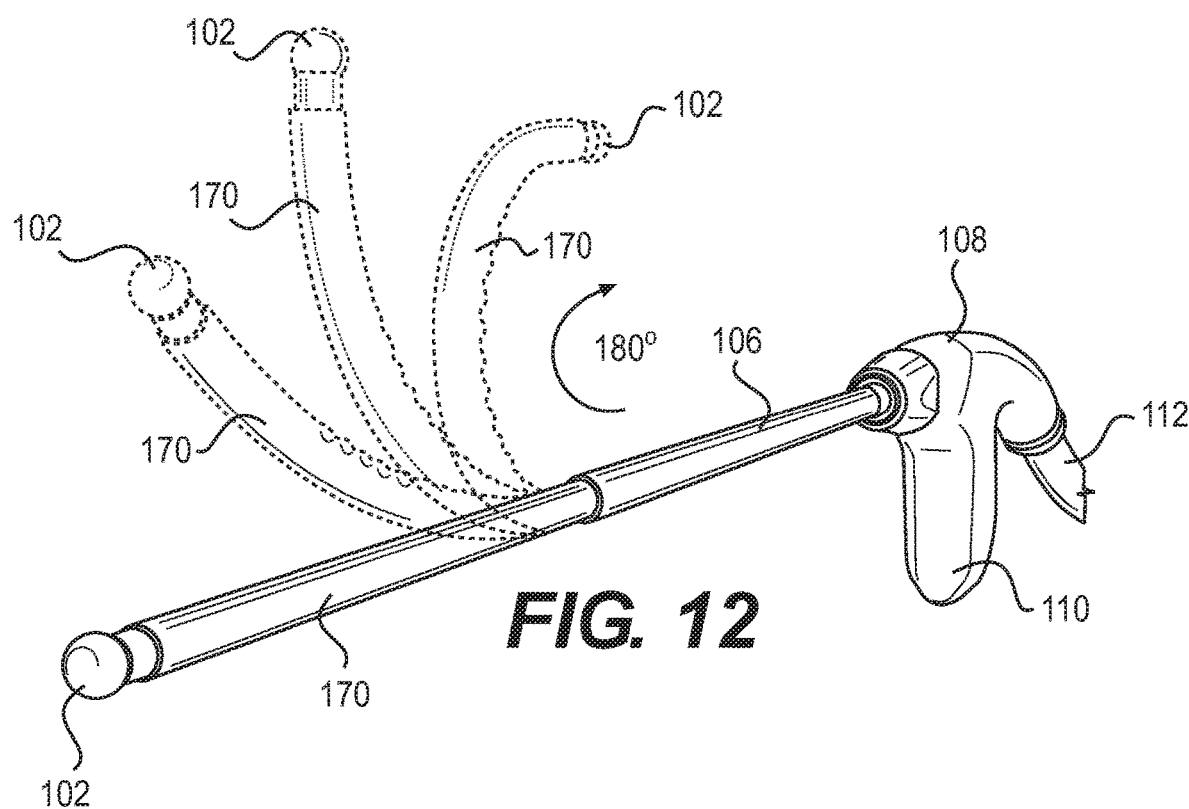
FIG. 12 an elevated perspective view of the first exemplary cryoprobe depicted with the ablation tip and insulated conduit in various bending positions.

As shown in FIG. 7, a longitudinal cross-section reflects the configuration within the insulated tube 106 and distally beyond where the insulated tube terminates. One or more thermocouples 160 may be positioned along the length of the malleable shaft 104 and in electrical communication with the thermocouple leads 118 to provide temperature measurements. In exemplary form, a thermocouple 160 may be soldered to an outside of the malleable shaft 104, yet be covered by the insulated tube 106. By way of further example, this thermocouple 160 may be partially embedded into the malleable shaft 104 and operative to provide temperature measurements specific to a fluid stream (exhaust or supply) flowing within the malleable shaft. By way of even further example, the thermocouple 160 may be offset from a distal end of the insulated tube between approximately one-half to three inches (including 1.34 inches), while other thermocouples may be arranged along the length of the insulated tube.

Continuing to refer to FIG. 7 and FIGS. 8-12, by way of example, the malleable shaft 104 may circumscribe the hypotube 136, which are both circumscribed by the insulated tube 106. Near a distal end of the insulated tube 106, the insulated tube 106 may be internally hollowed to provide a circumferential gap between the insulated tube and the malleable shaft 104. In this exemplary embodiment, this gap may be sized to receive a more flexible insulated conduit 170, where the longitudinal length of the gap may vary between approximately 0.1 inches to over 1.0 inches (including 0.32 inches). By way of example, this insulated conduit 170 may include a spacer 174 interposing a flexible cover 176 and the malleable shaft 104, which may maintain a thermally insulating gap (e.g., an air gap) between the flexible cover and the malleable shaft. In exemplary form, the spacer 174 may comprise one or more (e.g., four) helices 174a, 174b, 174c, and 174c (having generally constant, circular axial cross-sections and/or a common axial dimension) that are longitudinally offset that at any given axial cross-section, along the longitudinal length, the respective helices may be oriented respectively at 12 o'clock, 3 o'clock, 6 o'clock, and 9 o'clock. At each longitudinal end, the helices 174a, 174b, 174c, 174d may be coupled together or interface with a static structure to maintain the position of the segment ends. For example, each helix may comprise various non-conductive materials such as, without limitation, polymers such as thermoplastics. In some exemplary embodiments, an individual helix 174a, 174b, 174c, 174d may be formed as a hollow tube, which may optionally contain an insulative material. At a proximal end 175 of the insulated conduit 170, the outer diameter may be decreased or necked down 173 to allow insertion of the proximal end into the gap between the malleable shaft 104 and the distal end of the insulated tube 106. For example, the insulated conduit 170 may be necked down to have an outside dominant dimension less than the outer diameter of the helices 174a, 174b, 174c, 174d. Moving distally, the insulated conduit 170 may increase in outer diameter and include a proximal shoulder 180 against which a proximal end of the spacer 174 is seated. For example, the insulated conduit may comprise any insulating material with any number of configurations to provide vacuum or fluid gaps (e.g., stagnant fluid pockets) such as, without limitation, polystyrene foam. The insulated conduit 170 is operative to insulate the malleable shaft 104 from an external environment. In this exemplary embodiment, the malleable shaft 104, hypotube 136, and insulated conduit 170 may be flexible enough to allow more than 180 degrees of bend to reposition the ablation tip 102 between a starting position and an end position (see FIG. 12).

Figure 13:
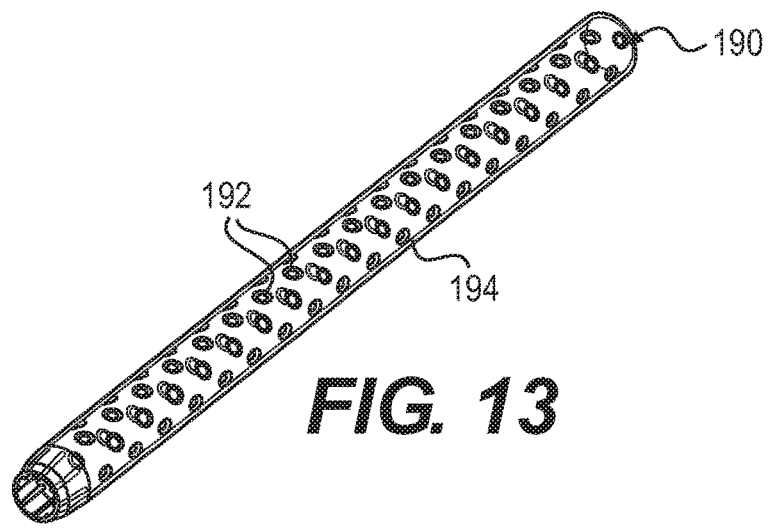
FIG. 13 is an elevated perspective view of a second exemplary insulated conduit in accordance with the instant disclosure.
Figure 14:
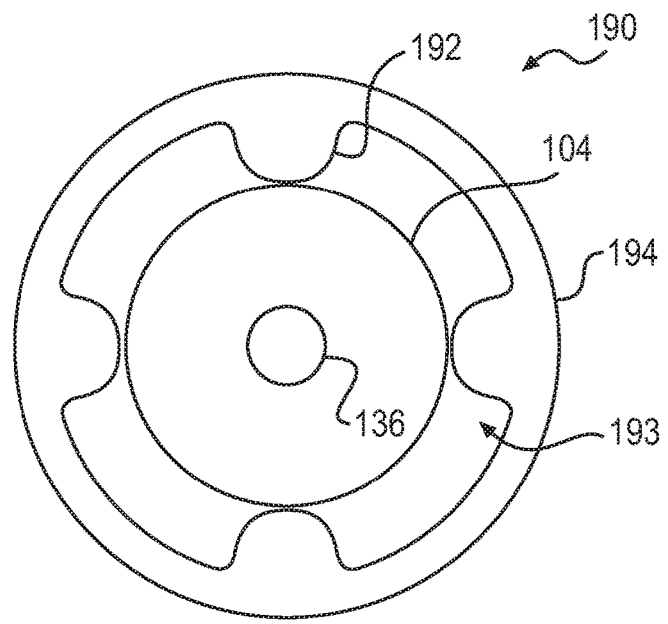
FIG. 14 is an axial cross-sectional view of the second exemplary insulated conduit circumscribing a malleable shaft and supply conduit.

Turning to FIGS. 13 and 14, an alternate exemplary embodiment may replace the foregoing insulated conduit 170 with an alternate exemplary a flexible covering 190 to circumscribe the malleable shaft 104 and hypotube 136. In exemplary form, the flexible covering 190 may include a plurality of interior protrusions 192 extending from an interior of a circumferential continuous cover 194, where the protrusions may be arranged in alternating circular and axial patterns along a longitudinal length. The arrangement of protrusions delineates air gaps (e.g., stagnant fluid pockets) 193 between the malleable shaft 104 and the continuous cover 194, which results in thermal insulation regardless of the whether the malleable shaft 104 is oriented linearly or embodies some arcuate shape indicative of being bent (see FIG. 12). Using an arrangement of protrusions 192, a greater volume of air spaces may be created in comparison to the foregoing insulated conduit 170. Moreover, by forming the protrusions 192 in a conical, frustoconical shape, or semispherical shape, the surface area in contact between the protrusions and the malleable shaft 104 for conductive heat transfer may be reduced. Those skilled in the art will understand that the shape and pattern of the protrusions may be altered to increase thermal insulative performance.

Figure 15:
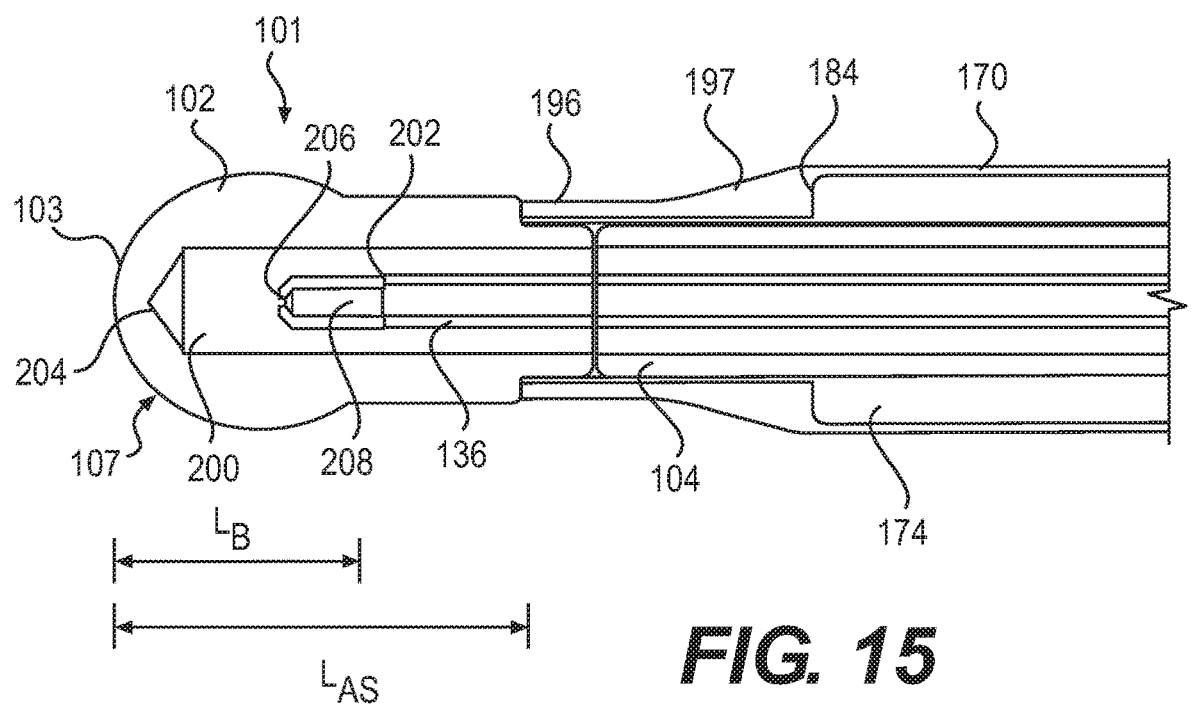
FIG. 15 is a longitudinal cross-sectional view of the first exemplary cryoprobe of FIG. 1 taken at a distal end thereof.
Figure 16:
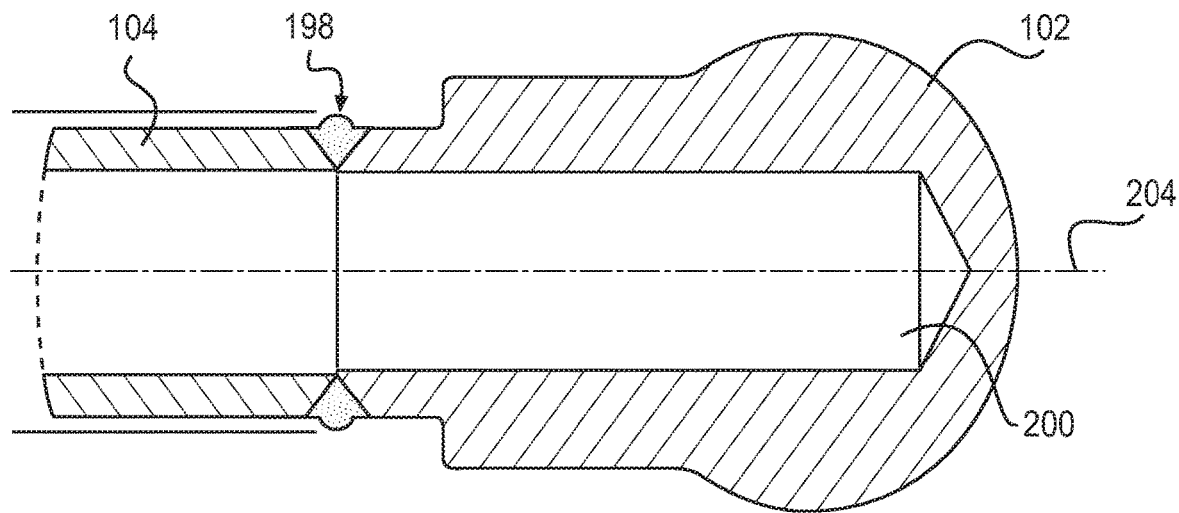
FIG. 16 is a longitudinal cross-sectional view of a malleable shaft being jointed to an ablation tip using a first exemplary mounting technique.
Figure 17:
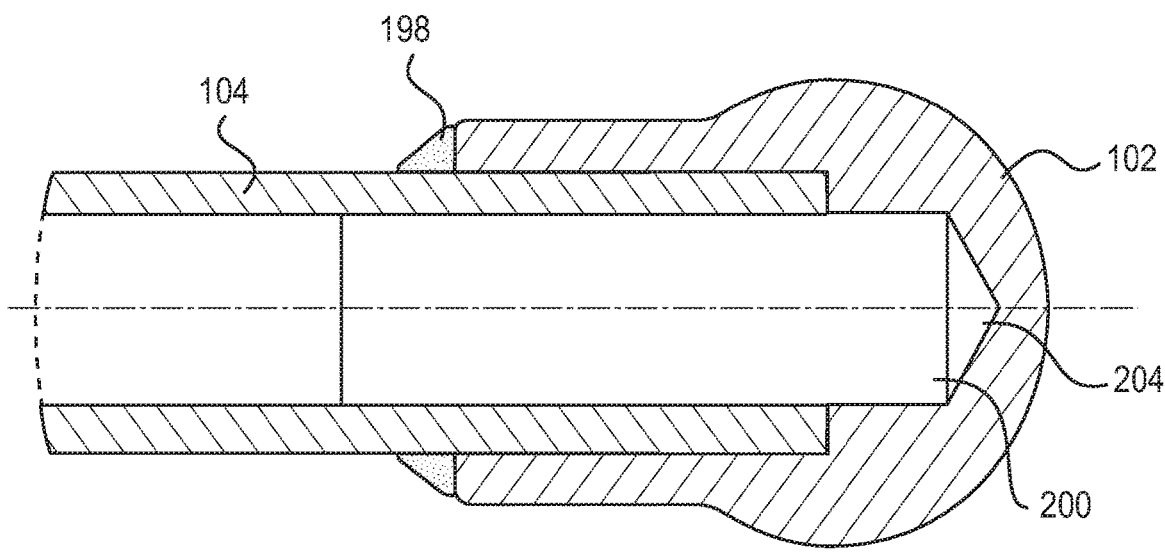
FIG. 17 is a longitudinal cross-sectional view of a malleable shaft being jointed to an ablation tip using a second exemplary mounting technique.

Referring to FIGS. 15-17, a distal end 196 of the flexible insulated conduit 170 may exhibit a decreased or necked down 197 outer diameter (as would the flexible covering 190 if used instead). For example, the insulated conduit 170 may be necked down to have an outside dominant dimension less than the outer diameter of the helices 174a, 174b, 174c, 174d. As part of the insulated conduit 170 decreasing in outside diameter, a distal shoulder 184 may be created internally upon which the distal end of the spacer 174 may be seated. Proximally inset from the distal end 196 of the insulated conduit 170, the malleable shaft 104 may terminate and be joined by way of a fluid tight seal to the ablation tip 102. By way of example, as depicted in FIG. 16, the fluid tight seal may be accomplished via a weld 198 at the joint location between the ablation tip 102 and the malleable shaft 104 such as, without limitation, a circumferential surface weld and a circumferential butt weld. Alternatively, as depicted in FIG. 17, the malleable shaft 104 may extend into a cavity formed into the ablation tip 102 and a fluid tight seal may be accomplished by a weld 198 at a lap joint such as, without limitation, a circumferential fillet weld. Those skilled in the art will fully understand that other forms of fluidically joining the malleable shaft 104 and the ablation tip 102 are contemplated herein and include, without limitation, chemical bonding (e.g., adhesives), brazing, welding (e.g., spin and friction welding), swaging, and mechanical connecting (e.g., threaded connections, friction fit, etc.).

Returning to FIG. 15, in exemplary form, the ablation tip 102 terminates at a closed distal end 103 and comprises a solid metal casing having an internal cavity 200 configured to receive a terminal end 202 of the hypotube 136 that extends beyond of the malleable shaft 104. In this exemplary embodiment, the metal forming the ablation tip 102 may comprise any metal or metal alloy usable in a surgical setting to include, without limitation, aluminum, titanium, stainless steel, copper, silver, gold, and any other thermally conductive metal or alloy, including coatings including one or more of the foregoing. By way of example, the cavity 200 may embody a cylindrical shape that conically tapers to a distal point 204. In this exemplary embodiment, the distal termination of the hypotube 136 comprises a nozzle 206 through which cryogenic fluid may be expelled and flow into the portion of the cavity 200 unoccupied by the hypotube. In exemplary form, the nozzle 206 may have a nozzle opening between 0.05 and 0.001 inches in diameter and be positioned from a distal end of the cavity 200 anywhere from 0.005 inches to 2.0 inches (including 0.100 inches). Though not required, the hypotube 136 may also include a fluid flow feature 208, such as upstream of the nozzle 206 (e.g., between the hypotube 136 and the nozzle 206), to vary the cross-sectional area available for cryogenic fluid to flow through the nozzle 206. By way of example, the hypotube 136 may be coupled to the fluid flow feature (e.g., a fluid flow constriction) 208 operative to decrease the cross-sectional area available for cryogenic fluid flow immediately proximal to the nozzle 206, which operates to increase the pressure of the cryogenic fluid at the nozzle in comparison to the pressure of the cryogenic fluid flowing upstream of the fluid flow feature. Generally, a nozzle 206 and/or fluid flow feature 208 may have a cross-section that is substantially less than the cross-section of the fluid supply conduit (e.g., hypotube 136) upstream from the termination of the fluid supply conduit. The nozzle may have a cross-section for fluid flow that is substantially less than the cross-section for fluid flow of the fluid flow feature 208.

In this exemplary embodiment, it is envisioned that the cryogenic fluid exiting the nozzle 206 is at a higher pressure upstream from the nozzle and is allowed to expand downstream of the nozzle within the cavity 200 at a significantly lower pressure, thereby creating a Joule-Thompson expansion and significantly lowering the temperature of the cryogenic fluid and the ablation tip 102. By way of example, the cryogenic fluid may comprise any number of cryogenic fluids such as, without limitation, nitrous oxide, argon, carbon dioxide, as well as phase change fluids. By way of further example, in the case of nitrous oxide, the cryogenic fluid may be supplied as a liquid at a temperature of 26.7 C and pressure of 800 psi upstream of the nozzle, and may comprise a gaseous phase or a mixed phase of gas and liquid at approximately 45 psi and −68 C within the ablation tip cavity 200. A countercurrent flow may be established by lower pressure cryogenic fluid flowing through the cavity 200 and around the hypotube 136 and continuing into and through the malleable shaft 104 to circumscribe the hypotube, thereby providing precooling to the cryogenic fluid flowing through the hypotube as Joule-Thompson expansion within the ablation tip 102 continues. Though not required, a vacuum or low-pressure purge may be drawn on the exhaust line 116 (see FIG. 1) to hasten the flow of expanded cryogenic fluid through the malleable shaft 104, through the exhaust adapter 140, and into the exhaust line. As Joule-Thompson expansion continues occurring at the ablation tip 102, the exterior of the tip 102 becomes cooled enough for use in an ablation procedure by bringing the tip into contact with tissue to be ablated. By way of example, depending upon the cryogen fluid utilized, exemplary flow rates for cryogenic fluid through the nozzle 206 range between approximately fifteen to greater than one hundred cubic centimeters per minute.

Figure 18:
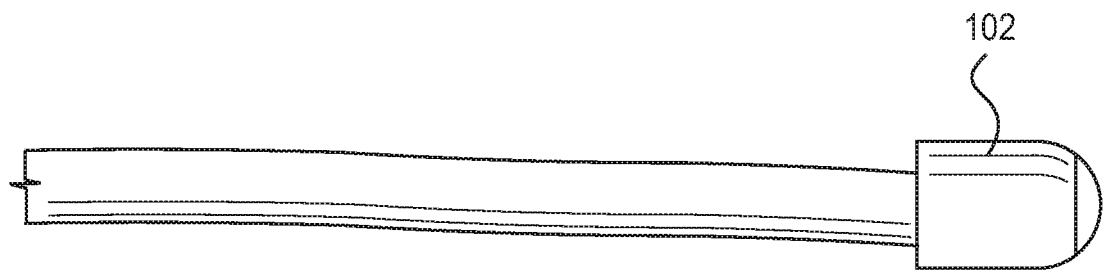
FIG. 18 is a profile view of an alternate exemplary ablation tip having a domed cylindrical shape.
Figure 19:
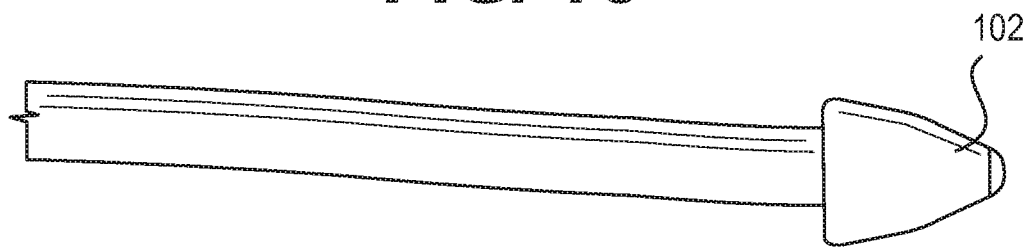
FIG. 19 is a profile view of a further alternate exemplary ablation tip having a rounded conical shape embodying a spherical contact surface.

Referring to FIGS. 15-19, in this exemplary embodiment, the ablation tip 102 may embody a bulbous distal exterior surface 107, such as a semi-spherical surface having diameters ranging between approximately 3.0 to 18.0 millimeters. Generally, as used herein, "bulbous" may refer to an enlarged (with respect to adjacent structure) and generally rounded exterior surface. Other exterior shapes and surfaces may be utilized for the ablation tip 102 such as, without limitation, a domed cylindrical surface as depicted in FIG. 18, and a rounded conical surface as depicted in FIG. 19, or any of other various bulbous surfaces known to those skilled in the art. For exterior surfaces other than spherical, the dominant axial dimension may be between 1.0 to 25 millimeters. By way of further example, the ablation tip 102 may embody any bulbous exterior surface. Those skilled in the art will understand that the exterior surface of the ablation tip 102 may be amenable to any number of exterior shapes specifically designed to perform specific ablation of certain anatomical features. In exemplary form, the ablation tip 102 may be necked down to include a proximal exterior surface with a substantially constant axial profile, the diameter of which is less than a diameter of the bulbous exterior. This necked down section may terminate at a step change in axial diameter to facilitate a fluid tight seal between the ablation tip 102 and the malleable shaft 104. Additionally, the ablation tip 102 may be attached and detached to the malleable shaft 104 with methods known in the art. Generally, in some exemplary embodiments, a bulbous distal exterior surface 107 of the distal ablation 101 section may extend for a longitudinal length LB, which may be at least half of a longitudinal length LAS of an exposed exterior surface of the distal ablation section. In other exemplary embodiments, the longitudinal length LB of the bulbous exterior surface 107 of the distal ablation section 101 may extend less than half of the longitudinal length LAS of the exposed exterior surface of the distal ablation section.

Figure 20:
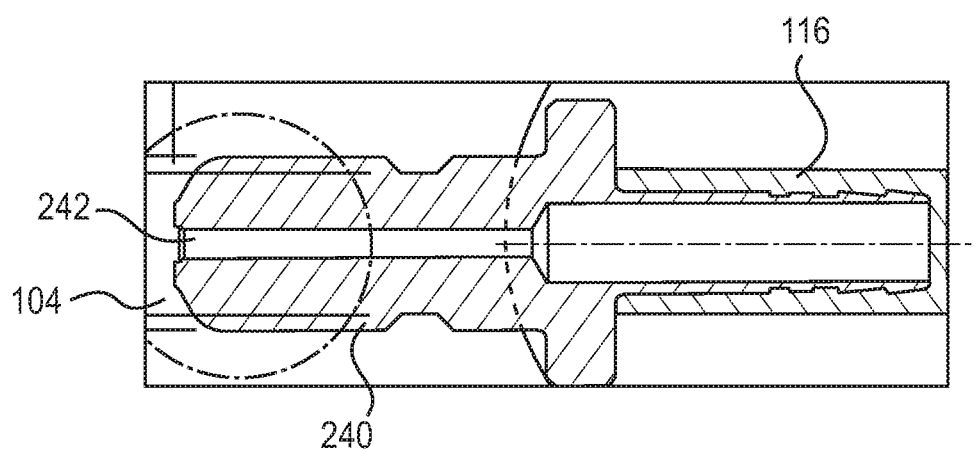
FIG. 20 is a longitudinal cross-sectional view of an alternate adapter that provides a fluid flow constriction that may be used in accordance with the instant disclosure to create backpressure at the ablation tip.

Referring to FIG. 20, an alternate exemplary adapter 240 including a flow restricting element may be used in place of the foregoing exemplary adapter 140 in order to throttle the exhaust flow of cryogen from the malleable shaft 104, thereby creating back pressure. In exemplary form, the temperature that the ablation tip 102 can achieve may be directly proportional to the back-pressure of the cryogen exhaust stream in that greater cryogen backpressure results in greater temperatures at the ablation tip. In exemplary form, a majority of heat removal may be the result of a phase change (boiling) of a cryogen within or near the ablation tip 102. The temperature that the ablation tip 102 can achieve is proportional to the boiling temperature (vaporization temperature) of the cryogen, which is proportional to the cryogen pressure. For example, as back pressure upon the cryogen is increased, so too does the temperature increase as to the lowest possible temperature the ablation tip can achieve. Without some sort of flow restricting element (e.g., a valve or throttle) to retard the flow of the cryogen exhaust stream, the back-pressure may become an inconsistent by-product of flow restrictions in the exhaust path since these flow restrictions may be flow-rate dependent. FIG. 20 depicts an exemplary flow restricting element in the form of a constriction 242 located between the exhaust cryogen flow coming from the malleable shaft 104 and ultimately flowing into the exhaust line 116. Given that the dimensions of the constriction 242 are of a fixed dimension with no valve, the amount of backpressure generated is a function of flow rate, with higher flowrates resulting in greater backpressures. In some example embodiments according to at least some aspects of the present disclosure, the adapter 140 may be constructed so that the constriction 242 has a cross-sectional area for cryogen exhaust flow that is a fraction of a cross-sectional area for cryogen exhaust flow of the exhaust line 116. In an exemplary embodiment, the cross-sectional area for cryogen exhaust flow of the constriction 242 may be less than about 70% of the cross-sectional area for cryogen exhaust flow of the exhaust line 116. In another exemplary embodiment, the cross-sectional area for cryogen exhaust flow of the constriction 242 may be less than about 50% of the cross-sectional area for cryogen exhaust flow of the exhaust line 116. In yet another exemplary embodiment, the cross-sectional area for cryogen exhaust flow of the constriction 242 may be less than about 30% of the cross-sectional area for cryogen exhaust flow of the exhaust line 116. In still another exemplary embodiment, the cross-sectional area for cryogen exhaust flow of the constriction 242 may be less than about 15% of the cross-sectional area for cryogen exhaust flow of the exhaust line 116. In another exemplary embodiment, the cross-sectional area for cryogen exhaust flow of the constriction 242 may be about 10% of the cross-sectional area for cryogen exhaust flow of the exhaust line 116.

Figure 21:
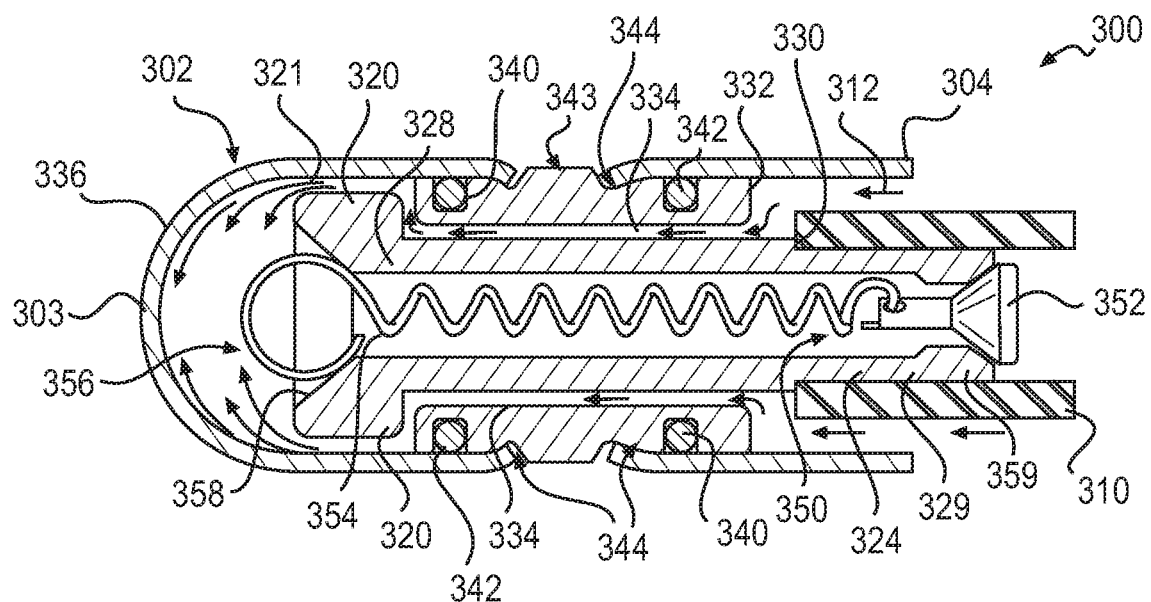
FIG. 21 is a longitudinal cross-sectional view of a second exemplary cryoprobe taken at a distal end thereof.

Referencing FIG. 21, a second exemplary cryogenic probe (cryoprobe) 300 may share many of the same components as the first exemplary cryoprobe 100 including the handle housing 108, connection bundle 112, supply line 114, exhaust line 116, thermocouple leads 118, and insulated tube 106. But where the second exemplary cryoprobe 300 differs is the configuration of the malleable shaft and ablation tip. In this exemplary embodiment, the malleable shaft 304 may or may not be covered with a flexible insulated conduit 170. Regardless of whether a flexible insulated conduit is utilized, the malleable shaft 304 may circumscribe a fluid exhaust conduit 310 to define a path for spent cryogen to be channeled to the handle housing 108. The outer circumference of the exhaust conduit 310 cooperates with an inner circumference of the malleable shaft 304 to delineate a fluid supply conduit 312 for cryogenic fluid. In exemplary form, the ratio of cross-sectional area of the exhaust conduit 310 to the supply conduit 312 may range between approximately 30:1 to 1:1. A significant difference with the instant exemplary cryoprobe piping is that the exhaust conduit 310 lies circumferentially inset from the supply conduit 312, as a means to avoid inadvertent ablation of tissue that may come in contact with the malleable shaft 304 given that the conditions of the cryofluid traveling through the supply conduit may not necessarily be cold enough to ablate tissue (e.g., above about −10 C). In exemplary form, the supply conduit 312 does not get cold enough to ablate tissue since the fluid flowing therethrough is at high pressure (e.g., 300 to 800 psi) so the boiling point of the cryofluid is above a tissue ablating temperature. Heat generated due to compressing the cryofluid also helps keep the outside of the supply conduit 312 above a tissue ablating temperature. In addition, any heat exchange from the exhaust tube into the cryofluid flowing through the supply conduit 312 will be pushed through the boiler 320 into the exhaust stream. A distal end of the malleable shaft 304 extends further distally than does the distal end of the exhaust conduit 310. This difference in distal termination provides a collared recess to partially receive a boiler 320 having an axial cross-section that matches that of the malleable shaft 304 which, in exemplary form, may be circular.

Figure 22:
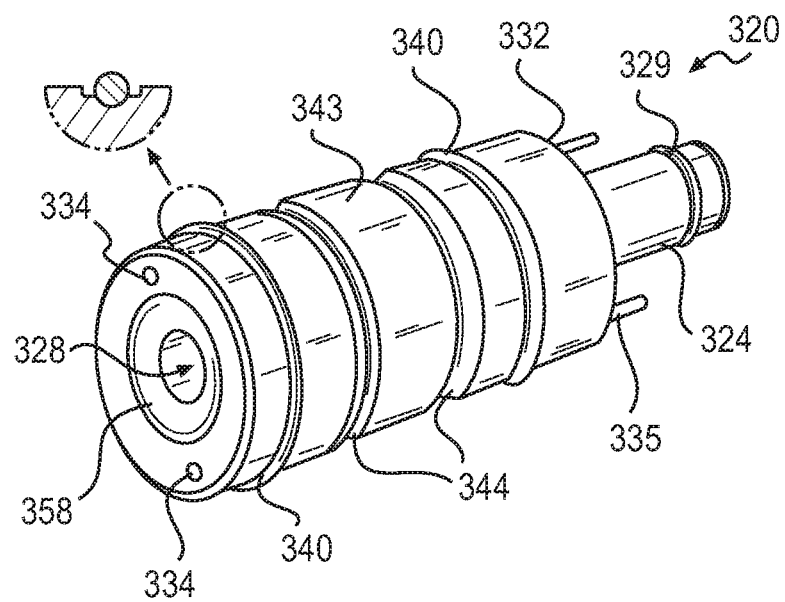
FIG. 22 is an elevated perspective view of an exemplary boiler that may be part of the second exemplary cryoprobe.
Figure 23:
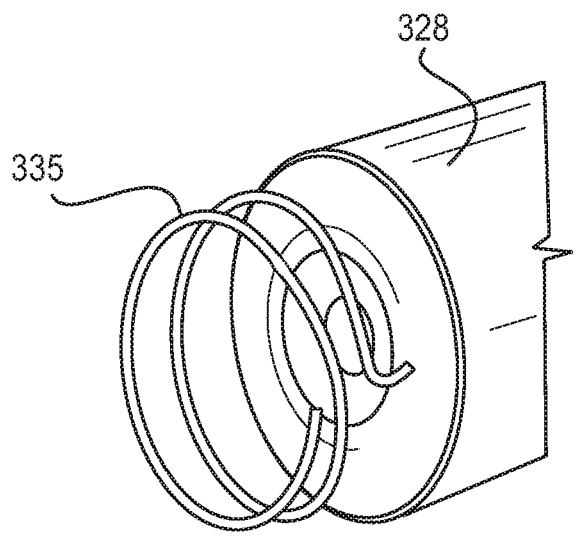
FIG. 23 is an elevated perspective view of the boiler of FIG. 22 shown in phantom and having at least one hypotube extending therefrom to delineate a fluid flow channel.

Referring to FIGS. 21 and 22, a proximal end of the boiler 320 may include a nipple 324 configured to be received within the exhaust conduit 310 to create a fluidic seal between a central bore 328 extending through the boiler 320 and the interior of the exhaust conduit 310. In further exemplary form, the nipple 324 may include an exterior raised circumferential ring 329 configured to create a friction fit and fluidic seal between the nipple 324 and the exhaust conduit 310 to maintain the relative longitudinal position of the boiler 320 with respect to the exhaust conduit 310. In order to prohibit over-insertion of the boiler 320 into the exhaust conduit 310, the nipple 324 includes a circumferential lip 330 against which the distal end of the exhaust conduit 310 may abut. In exemplary form, the nipple 324 may terminate distally into a proximal flange 332 configured to extend axially to fill the interior gap formed by the overhanging distal end of the malleable shaft 304. Despite filling this interior gap, the boiler 320 may be provided with one or more channels 334 providing fluid communication between the supply conduit 312 and an interior of a distal ablation section 302, which may comprise the ablation tip 336, which includes a closed distal end 303, and/or the boiler 320. In exemplary form, the boiler 320 may be fabricated from a polymer material and injection molded over one or more preexisting lines, such as hypotubes 335, to delineate the channels 334 and allow fluid communication therethrough. By way of example, the channels 334 may not extend substantially beyond a distal end of the boiler 320 body, thereby forming nozzles substantially flush with the boiler 320 body. Alternatively, the hypotubes 335 may extend substantially beyond a distal end of the boiler 320 body in a spiral or other configuration to allow expanded cryogen fluid within the ablation tip 336 to pre-cool the cryogen fluid before it exits the channels within the interior of the ablation tip (see FIG. 23).

By way of example, to fluidically seal off the ablation tip 336 and supply conduit 312 around the boiler 320, the boiler 320 may include two or more external circumferential trenches 340 that each receive a respective O-ring 342. Interposing the trenches 340 on the exterior circumference of the boiler 320 may be a raised rib 343 having counterpart furrows 344. In this exemplary embodiment, the height of the raised rib 343 may be chosen to be slightly less than the material thickness of at least one of the malleable shaft 304 and the ablation tip 336 so that, upon joining of the boiler 320, malleable shaft 304, and ablation tip 336, the resulting exterior surface of the joined components is not significantly uneven. In order to join the boiler 320, malleable shaft 304, and ablation tip 336 to one another, one may crimp down on the distal end of the malleable shaft 304 to position its end within a proximal one of the furrows 344, while a proximal end of the ablation tip 336 is similarly crimped down to be received within a distal one of the furrows 344. It should be noted that this crimping action taken with respect to the malleable shaft 304 and ablation tip 336 is also operative to complete formation of the fluid tight seal via the O-rings 342.

Formation of the fluid tight seal allows cryogen to flow from the supply conduit 312, through the channels 334 of the boiler 320, and into the interior of the ablation tip 336. Upon reaching the ablation tip 336, the cryogen fluid is allowed to expand within the interior of the ablation tip 336 at a significantly lower pressure, thereby creating a Joule-Thompson expansion and significantly lowering the temperature of the cryogenic fluid and ablation tip. By way of example, the cryogenic fluid may comprise any number of cryogenic fluids such as, without limitation, nitrous oxide, argon, and carbon dioxide. By way of further example, the cryogenic fluid may be a phase change fluid that is at equilibrium (or saturation point) at room temperature (about 15 C to 25 C) at pressure a pressure less than 2000 psi. By way of further example, in the case of nitrous oxide, the cryogenic fluid may be supplied as a liquid at a temperature of approximately 80° F. and pressure of approximately 800 psi upstream of the boiler 320, and may be exhausted as a gaseous phase or a mixed phase of gas and liquid at approximately 45 psi and −68 C. As Joule-Thompson expansion continues occurring within the ablation tip 336, the exterior of the ablation tip becomes cooled enough for use in an ablation procedure so that the ablation tip may be brought into contact with tissue intended to be ablated. By way of example, depending upon the cryogen fluid utilized, exemplary flow rates for cryogen fluid through the channels 334 range between approximately fifteen to greater than one hundred cubic centimeters per minute.

As previously discussed, the temperature an ablation tip 336 can achieve is directly proportional to the back-pressure of the cryogen exhaust stream. Accordingly, the second exemplary cryoprobe 300 may (or may not) include a flow restricting element in the form of a pressure (e.g., relief) valve 350 proximate the ablation tip 336 to maintain a predetermined backpressure within the ablation tip 336 by regulating the flow of spent cryogen though the exhaust conduit 310. In exemplary form, the relief valve 350 may include a frustoconical plug 352 operatively coupled to a spring 354 having a predetermined tension (i.e., spring rate). In this exemplary embodiment, the spring 354 may comprise a coil spring with an enlarged section 356 that is precluded from passing proximally beyond a distal frustoconical end 358 of the central bore 328. This distal frustoconical end 358 may also be operative to provide a funneling function for cryogen fluid exiting the ablation tip 336 interior and moving within the central bore 328. The tension of the spring 354 is preloaded (i.e., spring biased) to maintain engagement between the plug 352 and the frustoconical proximal end 359 of the central bore 328 (acting as a valve seat of a valve body) in a substantially fluid tight seal until reaching a predetermined pressure. When the fluid pressure within the central bore 328 reaches the predetermined pressure, the pressure of the cryogen exerts a force upon the plug 352 sufficient to overcomes the spring bias of the spring 354, thereby allowing separation between the plug 352 and frustoconical proximal end 359 of the central bore 328. By way of further example, those skilled in the art will understand that the spring 354 may be chosen or manipulated to set the backpressure maintained within the interior of the ablation tip 336. By way of still further example, the spring 354 may be chosen or manipulated to set the backpressure maintained within the interior of the ablation tip 336 to be between 15-100 psi (including between 30-50 psi). In exemplary form, for a central bore 328 having a diameter of 0.125 inches at its narrowest location, a spring force of 0.6 pound-force would be operative to maintain a 50 psi backpressure within the ablation tip 336. While the exemplary relief valve 350 has been described as extending into the boiler 320 and proximate the ablation tip 336, those skilled the art will understand that one or more relief valves may be positioned proximal to the boiler and/or not proximate to the ablation tip 336.

Regardless of the presence or absence of the relief valve 350, a countercurrent flow is established by expanded cryogenic fluid flowing through the central bore 328 and into the exhaust conduit 310 providing precooling to the cryogenic fluid flowing through supply conduit 312 and channel(s) 334 as Joule-Thompson expansion within the ablation tip 336 continues. The gap 321 between the exterior radial surface at the distal end of the boiler 320 and the radially interior surface of the ablation tip 336 may act as a nozzle, similar to nozzle 206 of cryoprobe 100. Similarly, channels 334 may act as a fluid flow constriction similar to fluid flow feature 208 of cryoprobe 100. In some example embodiments, the cross-section of the gap (nozzle) 321 may be substantially less than the cross-section of the supply conduit 312 upstream of the boiler 320. Similarly, in some example embodiments, the cross-section of the channels 334 may be substantially less than the cross-section of the supply conduit 312 upstream of the boiler 320. In some example embodiments, the cross-section of the gap (nozzle) 321 may be less than the cross-section of the channels 334. Though not required, a vacuum or low-pressure purge may be drawn on the exhaust line 116 (see FIG. 1) to hasten the flow of low-pressure cryogenic fluid through the exhaust conduit 310 and into the exhaust line.

In this exemplary embodiment, the ablation tip 336 may embody an exterior spherical shape having diameters ranging between approximately 3.0 to 18.0 millimeters. However, other exterior shapes may be utilized for the ablation tip 336 such as, without limitation, a domed cylindrical shape as depicted in FIG. 18, and a rounded conical shape as depicted in FIG. 19. By way of further example, the ablation tip 336 may embody any bulbous exterior shape (e.g., as shown in FIG. 15). Those skilled in the art will understand that the exterior shape of the ablation tip 336 may be amenable to any number of exterior shapes specifically designed to perform specific ablation of certain anatomical features.

Figure 24:
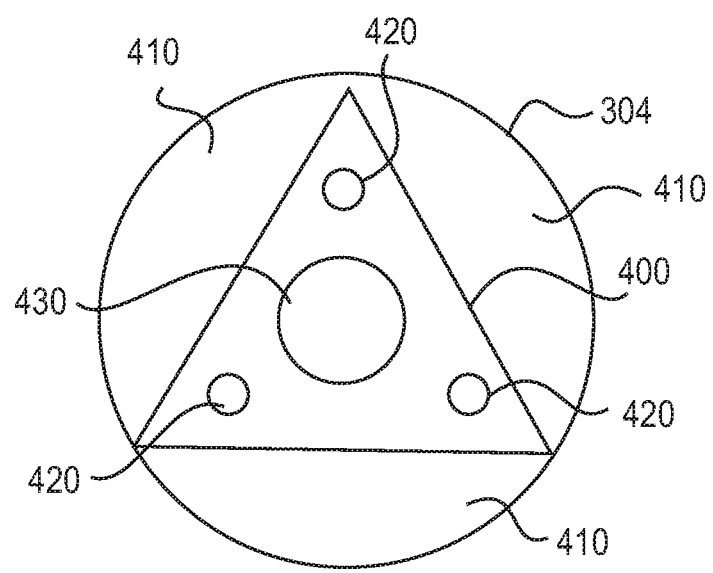
FIG. 24 is an axial cross-sectional view of a malleable shaft with a first exemplary longitudinal insert having a triangular shape with separate fluid flow paths therein and dedicated air pockets along the longitudinal length thereof.
Figure 25:
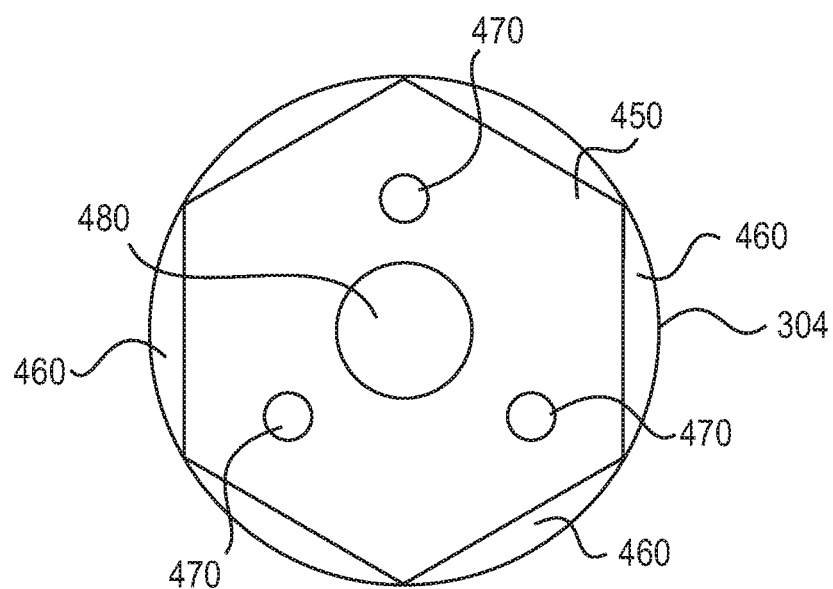
FIG. 25 is an axial cross-sectional view of a malleable shaft with a first exemplary longitudinal insert having a hexagonal shape with separate fluid flow paths therein and dedicated air pockets along the longitudinal length thereof.

Referring to FIGS. 24 and 25, those skilled in the art will likewise understand that various configurations may be utilized within the malleable shaft 304 to deliver cryogenic fluid to the ablation tip 336 and carry away expanded/cooled cryogenic fluid from the ablation tip 336. By way of example, looking specifically to FIG. 24, the malleable shaft 304 may house an insert 400 that delineates insulating air pockets (e.g., stagnant fluid pockets) 410, one or more cryogenic supply conduits 420, and one or more cryogenic exhaust conduits 430. The supply conduits 420 may be separate from the exhaust conduits 430. The exemplary insert 400 may comprise an extruded polymer such as, without limitation, polypropylene, polyvinylidenefluoride, and low-density polyethylene. The insert 400 may embody a triangular shape (e.g., cross-section) to provide three contact points on the interior of the malleable shaft 304 and reduce those points of contact between the insert and malleable shaft, thereby reducing conductive heat transfer between the relative cool exhaust conduit 430 and the surface of the malleable shaft 304. By way of further example, triangular shapes may be chosen to fit within the diameter of the malleable shaft 304 and provide three points of contact between the insert and shaft, realizing that an equilateral triangle provides the least amount of dead air volume, whereas a right triangle may provide the most amount of dead air volume. In some example embodiments, the dead air volume may be sealed and evacuated, which may provide a greater barrier to heat transfer to the outside surfaces. Alternatively to a triangular shape, additional sided shapes may be used (e.g., shapes with cross-sections having four or more sides). In exemplary form, the supply conduits 420 and exhaust conduit 430 may comprise nothing other than longitudinal channels formed within the insert 400 or may comprise dedicated tubing (such as hypotubes) that the insert is extruded around. It is also within the scope of this exemplary insert 400 to include one or more conduits for routing thermocouple leads (not shown) or sensor leads (not shown) so as to provide real-time information regarding temperature and/or pressure within one or more of the conduits 420, 430 and air pockets 410.

FIG. 25 depicts a further exemplary insert 450 that, may be positioned within the malleable shaft 304, and may delineate insulating air pockets (e.g., stagnant fluid pockets) 460, one or more cryogenic supply conduits 470, and one or more cryogenic exhaust conduits 480. The exemplary insert 450 may comprise an extruded polymer such as, without limitation, polypropylene, polyvinylidenefluoride, and low-density polyethylene. The insert 450 may embody a hexagonal shape to provide six contact points on the interior of the malleable shaft 304 and reduce those points of contact between the insert and malleable shaft, thereby reducing conductive heat transfer between the relative cool exhaust conduit 480 and the surface of the malleable shaft. By way of further example, by utilizing an object having a pointed (low surface area contact) contact with the malleable shaft, the surface area for conductive hear transfer is reduced in comparison to an arcuate surface matching the interior curvature of the malleable shaft. In exemplary form, the supply conduits 470 and exhaust conduit 480 may comprise nothing other than longitudinal channels formed within the insert 450 or may comprise dedicated tubing that the insert is extruded around. It is also within the scope of this exemplary insert 450 to include one or more conduits for routing thermocouple leads (not shown) or sensor leads (not shown) so as to provide real-time information regarding temperature and/or pressure within one or more of the conduits 470, 480 and air pockets 460.

One or more of the components disclosed herein may include an echogenic coating to allow for ultrasound visibility during a surgical procedure where direct line of sight may be obstructed. Those skilled in the art will understand the use of ultrasound for non-line of sight surgical procedures and therefore a detailed discussion of ultrasound has been omitted in furtherance of brevity. Alternatively to ultrasound, other methods of visualization known in the art may be used.

The foregoing cryoprobes 100, 300 may also include electrical sensing to indicate the ablation sequence is completed. By way of example, one may pulse (i.e., send an electrical signal through) a nerve or other tissue distal to an ablation, such as in the intercostal space during a cryoanalgesia procedure, and attempt to measure an electrical signal at a location proximal of the ablation, which ablation should dissipate the electrical signal or render it unmeasurable on account of the electrical signal being disrupted by the ablation. Continuous or discontinuous pulsing may be utilized to discern when the ablation procedure is complete.

Figure 26:
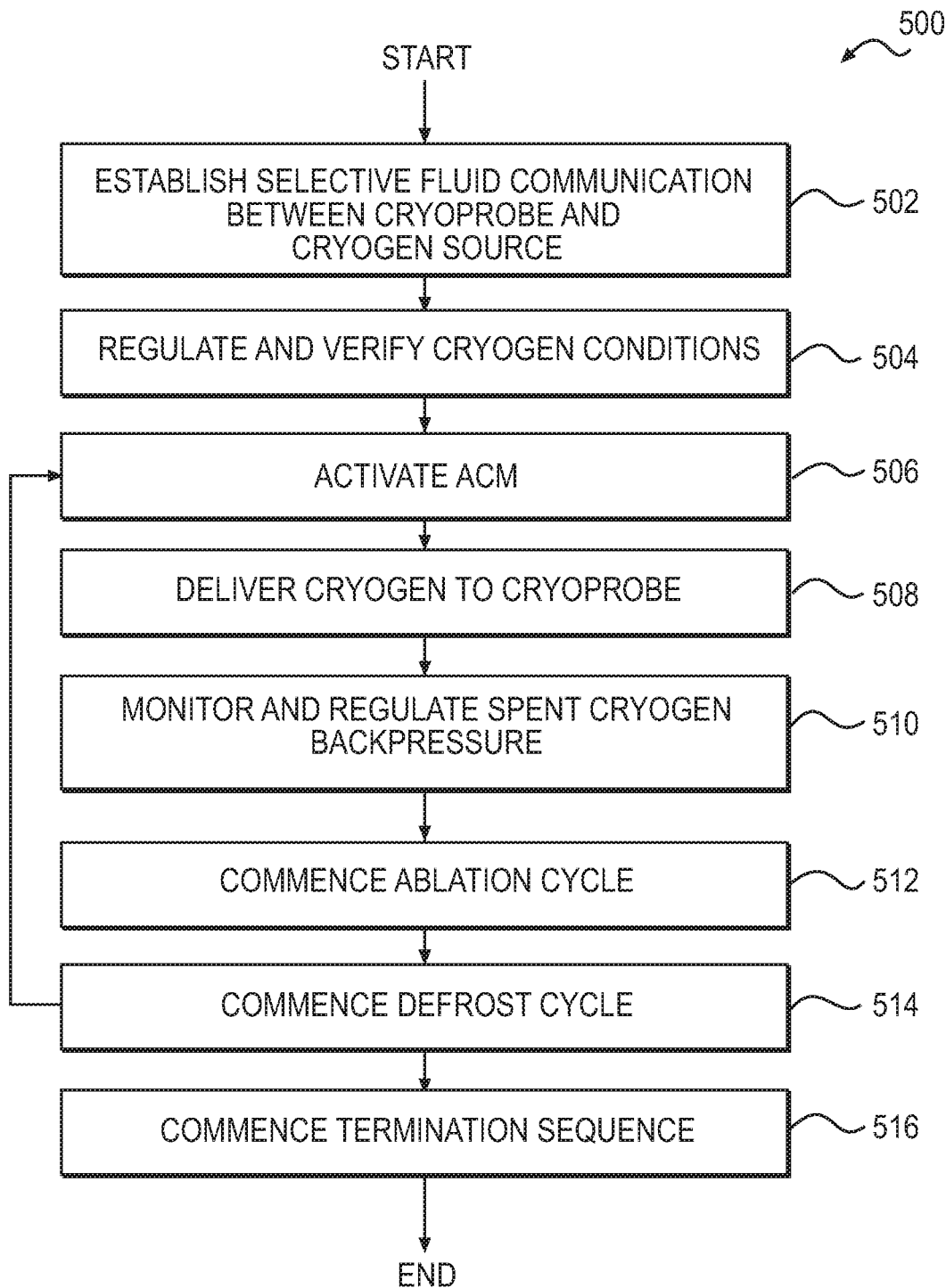
FIG. 26 is a process flow diagram depicting an exemplary process for utilizing one or more of the exemplary cryoprobes of the instant disclosure.

Turning to FIG. 26, an exemplary process 500 for using any of the foregoing cryoprobes 100, 300 is discussed hereafter. As a prefatory matter, a supply of cryogenic fluid needs to be established 502 from a static location or from a portable fluid holding container. By way of example, in an exemplary context of using nitrous oxide as the cryogenic fluid, a portable fluid holding container of liquified nitrous oxide (e.g., a 20 pound tank) may be fluidically connected to an AtriCure Cryo Module (ACM) that is itself fluidically connected to the cryoprobe 100.

In exemplary form, the ACM may be intended for use in the cryosurgical treatment of cardiac arrhythmias. The ACM may comprise a non-sterile, reusable device cryo ablation probe and/or a sterile, single use device cryo-ablation probe. The ACM may further include an electro-mechanical cryogenic surgical unit (that may include controls, displays, indicators, and associated programmed logic or circuitry) that delivers a cryogenic fluid (e.g., nitrous oxide ($N_2O$)) to a cryo ablation probe under conditions to cool an active region of the probe that is operative to ablate tissue coming into contact with the active region while the cryogenic fluid flows through the probe, which in exemplary form allows an operator to create lines of ablation through tissue such as, without limitation, cardiac tissue. The ACM may further include a cryogenic fluid holding container, a cryogenic fluid supply line in fluid communication (or selective fluid communication) with the holding container and cryo ablation probe, a cryogenic fluid exhaust line in fluid communication with the cryo ablation probe, a holding container heater, and a manual switch allowing control of delivery of cryogenic fluid from the holding container and to the cryo probe, as well as the cryo probe itself. In exemplary form, ACM provides controlled delivery of cryogenic fluid to the cryo probe to allow tissue lesion formation below −40° C., with typical operating ranges between −50° C. to −70° C.

In operation 504, cryogen conditions may be regulated and/or verified. In exemplary form, the portable fluid holding container may have a heater blanket covering the tank this is operative to add heat to the container to control the internal pressure, which in exemplary form may range between approximately 700 psi (−17° C.) and 850 psi (−23° C.). By way of example, the ACM may provide visual feedback regarding the pressure and temperature of the container, which is updated in real-time. To the extent heat is needed to reach the proper pressure, a green light may illuminate as part of the ACM to signify that the cryogen tank pressure is within a predetermined operating range.

In operation 506, a user may activate the ACM to deliver pressurized cryogenic fluid via a supply line to the cryoprobe. By way of example, the ACM may deliver pressurized cryogenic fluid at approximately 725 psi to the inlet connections of the cryoprobe so that just prior to reaching the ablation tip, the pressure of the cryogenic fluid is between 500 and 725 psi.

In operation 508, cryogen may be delivered to the cryoprobe 100, 300. Upon initial delivery of cryogenic fluid into the ablation tip, the cryogenic fluid expands to approximately atmospheric pressure (14.7 psi). In operation 510, the backpressure of the spent cryogen may be monitored and/or regulated. In exemplary form, as more cryogenic fluid enters the ablation tip and spent cryogenic fluid accumulates, backpressure begins to form and may be regulated to reach a steady state backpressure of approximately 52 psi, which corresponds to an ablation tip temperature of approximately −65° C. It should be noted, however, that using the ablation tip to ablate tissue may commence after the temperature of the ablation tip reaches a predetermined value, which may be above the steady-state temperature, including, without limitation, −40° C.

In operation 512, an ablation cycle may be commenced. Upon the ablation tip reaching the predetermined ablation temperature, the ACM may perform an ablation cycle where the ablation tip is maintained at or below the predetermined ablation temperature for a predetermined time, such as, without limitation, 120 seconds.

In operation 514, a defrost (e.g., warming) cycle may be commended. In exemplary form, upon completion of the ablation cycle, the ACM may activate the defrost cycle. By way of example, the defrost cycle may include blocking the flow of exhausted cryogenic fluid coming from the cryoprobe while continuing to supply cryogenic fluid to the cryoprobe. Eventually, the cryogenic fluid within the probe is all at the same pressure and temperature, such as, without limitation, approximately 800 psi (corresponding to an ablation tip temperature of approximately 10° C. Notably, various exemplary cryoprobes according to at least some aspects of the present disclosure may be constructed to withstand pressures expected during defrost cycles, which may be higher than pressures expected during freezing cycles. The ACM monitors the temperature at the ablation tip using a thermocouple and, upon reaching a predetermined defrost temperature, discontinues inlet flow of cryogenic fluid to the cryoprobe while allowing venting of the exhausted cryogenic fluid, eventually increasing the temperature and decreasing the pressure of the cryoprobe to atmospheric conditions.

Post termination of the defrost cycle, the ACM may be activated (operation 506) again to restart a freezing and defrost cycle. Alternatively, a procedure termination sequence (operation 516) may be initiated where connections between the cryoprobe and tank are discontinued and the ACM is deactivated.

Figure 28:
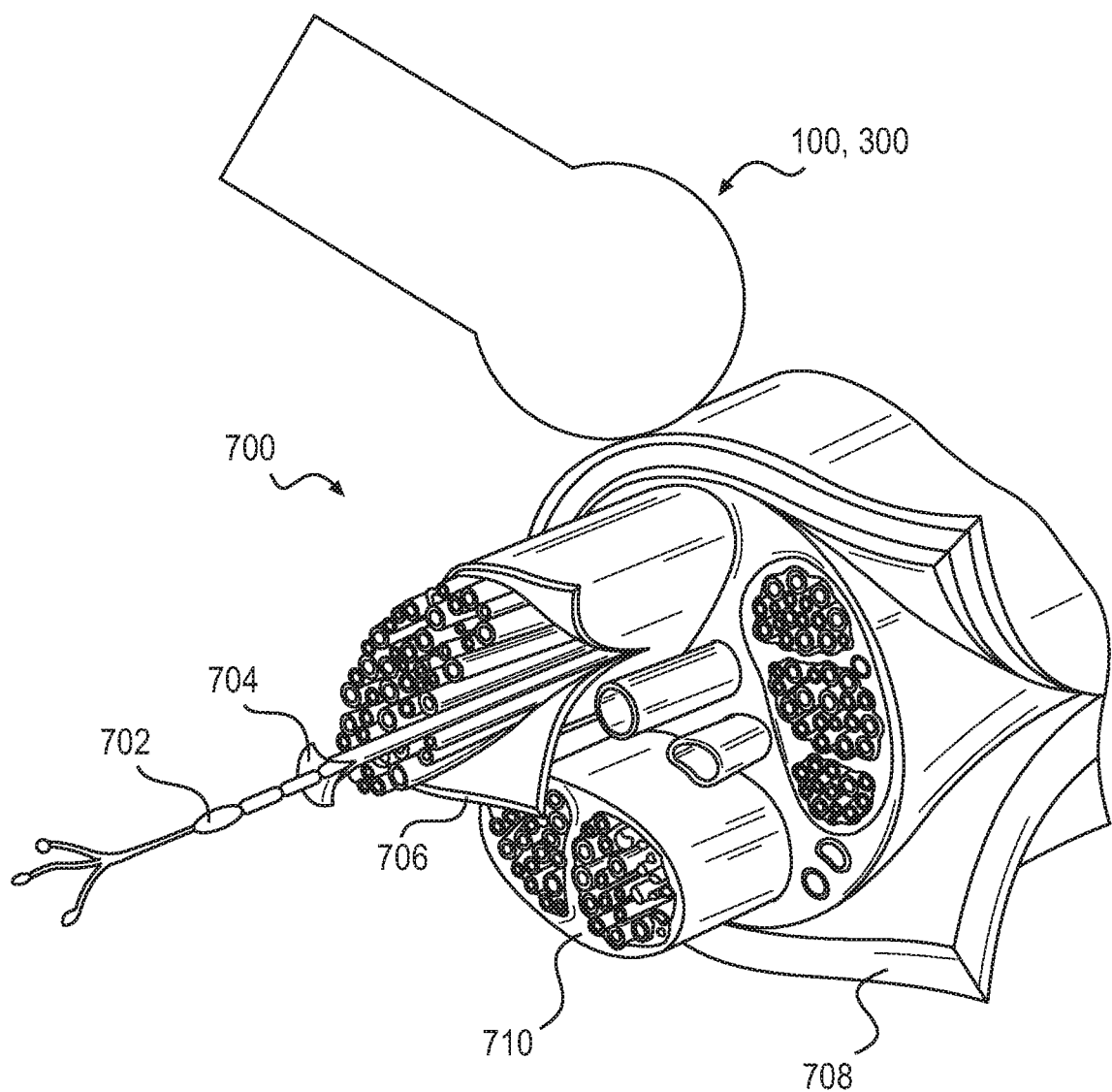
FIG. 28 is a cutaway perspective view of a nerve undergoing cryoanalgesia by a cryoprobe according to at least some aspects of the present disclosure.

Referring to FIG. 28, the exemplary cryoprobes 100, 300 may also be used in an application for cryoanalgesia. Cryoanalgesia, or freezing of nerves 700, uses extreme cold to ablate peripheral nerves and create a temporary yet fully recoverable loss of sensory nerve function. Cryoanalgesia causes axonotmesis, a level of nerve injury according to Seddon's classification in which the axons 702 and the myelin are disrupted but at least some of the surrounding tubular structures, such as the endoneurium 704, perineurium 706, fascicle 710, and/or epineurium 708, remain intact. The ensuing Wallerian degeneration, a process in which the entire length of the nerve segment distal to the cryoanalgesia site (cryolesion) is dismantled, takes approximately 1 week. Regeneration of the nerve begins from the proximal segment and continues at an average rate of 1-3 mm/day, following the intact structural components until the tissue is reinnervated. This process can take weeks to months depending on how significant the cryolesion is on the tissue. Because it preserves the structure of the nerve, cryoanalgesia has not been associated with development of neuromas.

Local analgesia to a nerve (e.g., intercostal nerve) is intended for managing pain due to the incision, any surgical muscle disruption, discomfort from nerve impingement by the surgical equipment (e.g., retractors) and surgical retainers (e.g., sutures), and for any opening created by a tube or trocar site. In exemplary form, one exemplary process comprises cryoanalgesia for post-thoracotomy pain that includes cryoablation of the intercostal nerves. Cryoablation attempted at temperatures not cold enough, for example, warmer than −20° C., will produce only transient nerve conduction block with a return to sensation upon tissue thawing, whereas temperatures too cold, for example colder than −100° C., can induce permanent nerve damage. When placed against tissue, such as the pleura or intercostal nerve, an ice ball may form around the tip of the cryoprobe 100, 300 and heat withdrawal may penetrate the tissue by several millimeters to create the cryolesion. In addition to the probe temperature, the extent of the cryolesion may depend on a number of other factors, including the size and material of the cryoprobe, the duration of the freeze, the rate of freeze, the thaw rate, and the number of freeze-thaw cycles. What follows is an exemplary procedure for conducting a cryoanalgesia responsive to a thoracotomy that is effective for pain management and may be applied to any nerve within an animal body.

Figure 27:
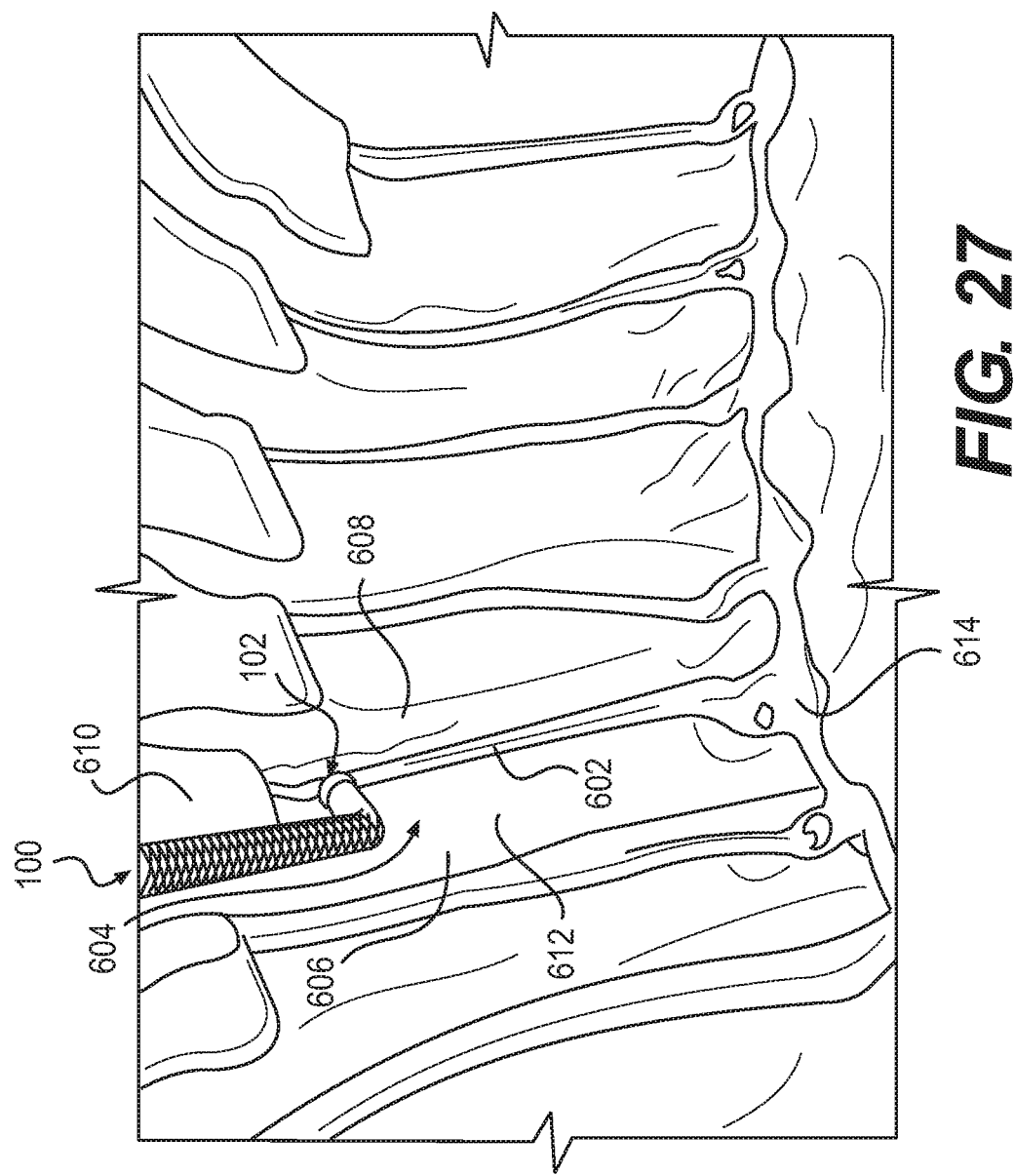
FIG. 27 is a graphical depiction of the ribcage and associate tissue showing positioning of a cryoprobe as part of a cryoanalgesia procedure for the intercostal region.

Referring to FIG. 27, it may be recommended to perform the cryoablation procedure as early as possible in the procedure, such as prior to or immediately following creation of the thoracotomy. The target nerve, such as an intercostal nerve 602, may be located in the incisional intercostal space 604 (e.g., between ribs 606, 608), preferably at the margin of the innermost intercostal muscle 610 and the membranous portion 612 of the internal intercostal muscle. A location may be chosen that is proximal to the lateral cutaneous branch but at least 2 cm from the ganglia 614 and 4 cm from the spine.

Approximately, 2-3 cm of the cryoprobe 100, 300 (including the ablation tip 102) may be exposed, where the elongated shaft may be shaped with a curve for the costal groove. A hockey stick or C-shape may be used. The ablation tip 102 of the cryoprobe 100, 300 may be placed directly on top of the nerve 602 with a slight angulation that assures the nerve is directly under the ablation tip. The insulated tube of the cryoprobe 100, 300 may be positioned on the rib 606, 608 and carefully slid down the rib until the cryoprobe falls off the rib into the costal groove.

Prior to ablation, the ablation tip 102 may be pressed into the costal groove with enough pressure to create compression of the tissue for stability and reduced local perfusion. Adequate pressure may be pressure sufficient to create blanching if depressed against the skin. Post locating the ablation tip 102 to contact the nerve 602 or in close proximity thereto, cryogenic fluid flowing through the cryoprobe 100, 300 is operative to cool the ablation tip (to approximately −65 C) and initiate or continue a freeze duration to freeze the nerve. By way of example, the freeze duration may be 120 seconds if the cryoprobe tip 102 is positioned in proximity to the nerve 602, whereas the freeze duration may be less (e.g., 90 seconds) in cases where the ablation tip is in direct contact with the nerve. The cryoprobe 100, 300 may be defrosted post freeze duration to allow disengagement between the ablation tip and the animal tissue. In exemplary form, as the cryoprobe 100, 300 defrosts, the ablation tip 102 may turn bright and shiny and may be moved without resistance. To prevent tissue or nerve damage, the cryoprobe should not be forcibly moved while adhered to tissue. Post defrost, the freeze duration process and defrost sequence may be repeated at another location of the same nerve (or at a different location of a different nerve) and repeated as necessary to achieve the proper pain management result. In general, some exemplary cryoanalgesia procedures as described above may be repeated on the intercostal nerves located in each of the third to ninth intercostal spaces.

In the cardiac space, it may be difficult to place an ablation tip from conventional cryoprobes that are known in the art. With the exemplary ablation tip 102, ablation of the nerve in the thoracic space may be easily accomplished by providing better contact on the nerve. Additionally, less ablations may be required due to the size of the tip.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A cryogenic probe comprising:
    an elongated shaft at least partially housing or delineating a fluid supply conduit and a fluid exhaust conduit, the elongated shaft including a distal ablation section terminating at a closed distal end;
    a housing at least partially circumscribing at least a portion of a proximal end of the elongated shaft and receiving or delineating at least a portion of the fluid supply conduit and a portion of the fluid exhaust conduit;
    a boiler comprising one or more channels providing fluid communication between the fluid supply conduit and an interior of the distal ablation section, the boiler comprising a central bore creating a fluid seal with an interior of the fluid exhaust conduit; and
    a valve extending into the boiler and in fluid communication with the fluid exhaust conduit and downstream from the distal ablation section, the valve configured to vary the flow of fluid through at least a portion of the fluid exhaust conduit;
wherein the valve comprises a valve plug configured to engage a valve seat and form a seal therebetween; and
wherein the valve plug is spring-biased to engage the valve seat.

2. The cryogenic probe of claim 1, wherein the valve includes a variable constriction.

3. The cryogenic probe of claim 2, wherein a cross-sectional area for fluid flow of the variable constriction is operative to be less than about 70% of a cross-sectional area for fluid flow of the exhaust line.

4. The cryogenic probe of claim 2, wherein a cross-sectional area for fluid flow of the variable constriction is operative to be less than about 50% of a cross-sectional area for fluid flow of the exhaust line.

5. The cryogenic probe of claim 2, wherein a cross-sectional area for fluid flow of the variable constriction is operative to be less than about 30% of a cross-sectional area for fluid flow of the exhaust line.

6. The cryogenic probe of claim 2, wherein a cross-sectional area for fluid flow of the variable constriction is operative to be less than about 15% of a cross-sectional area for fluid flow of the exhaust line.

7. The cryogenic probe of claim 2, wherein a cross-sectional area for fluid flow of the variable constriction is operative to be about 10% of a cross-sectional area for fluid flow of the exhaust line.

8. The cryogenic probe of claim 1, wherein the distal ablation section includes a bulbous exterior surface having a radial diameter maximum interposing lesser radial diameters.

9. The cryogenic probe of claim 1, wherein the distal ablation section includes a necked down section to vary a cross-section of the distal ablation section.

10. The cryogenic probe of claim 1, wherein at least a portion of the fluid supply conduit extends into the distal ablation section.

11. The cryogenic probe of claim 10, wherein at least the portion of the fluid supply conduit extending into the distal ablation section includes a fluid flow constriction prior to reaching a nozzle within the distal ablation section.

12. The cryogenic probe of claim 1, wherein a proximal aspect of the distal ablation section is fluidically sealed to a distal aspect of the elongated shaft using at least one of an adhesive bond and a weld.

13. The cryogenic probe of claim 1, further comprising a flexible insulated conduit circumscribing the elongated shaft along at least a portion of its longitudinal length.

14. The cryogenic probe of claim 13, wherein the flexible insulated conduit circumscribes the elongated shaft along a majority of its longitudinal length.

15. The cryogenic probe of claim 13, wherein the flexible insulated conduit includes a spacer interposing an outer cover of the flexible insulated conduit and an exterior of the elongated shaft.

16. The cryogenic probe of claim 15, wherein the spacer comprises a foam.

17. The cryogenic probe of claim 15, wherein the spacer comprises a helix.

18. The cryogenic probe of claim 15, wherein the spacer comprises a plurality of polymer helices.

19. The cryogenic probe of claim 18, wherein:
the polymer helices are longitudinally offset from one another along the flexible insulated conduit; and,
each of the polymer helices has a common axial dimension.

20. The cryogenic probe of claim 15, wherein the spacer terminates before reaching at least one of a proximal end and a distal end of the flexible insulated conduit.

21. The cryogenic probe of claim 17, wherein the flexible insulated conduit is necked down to have an outside dominant dimension less than an outer diameter of the helix at at least one of a proximal end and a distal end of the flexible insulated conduit.

22. The cryogenic probe of claim 1, wherein the elongated shaft provides greater than 180 degrees of bending without fracturing.

23. The cryogenic probe of claim 1, wherein an interior of the elongated shaft and an exterior of the fluid supply line delineate the fluid exhaust conduit.

24. The cryogenic probe of claim 1, wherein an interior of the elongated shaft and an exterior of the fluid exhaust line delineate the fluid supply conduit.

25. The cryogenic probe of claim 8, wherein the bulbous exterior surface extends longitudinally more than half of a longitudinal length of an exposed exterior surface of the distal ablation section.

26. The cryogenic probe of claim 8, wherein the bulbous exterior surface extends longitudinally less than half of a longitudinal length of an exposed exterior surface of the distal ablation section.

27. The cryogenic probe of claim 8, wherein the distal ablation section is configured to withstand a pressure during a warming operation which includes blocking the flow of the fluid through the fluid exhaust conduit.

28. The cryogenic probe of claim 1, wherein the housing includes an interior cavity housing an adapter operative to change coaxial orientation of the fluid supply conduit and the fluid exhaust conduit to parallel orientation.

29. A cryogenic probe comprising:
a malleable elongated shaft at least partially housing or delineating a fluid supply conduit and a fluid exhaust conduit;
a flexible insulated conduit circumscribing the malleable elongated shaft along a majority of its longitudinal length and extending distally beyond the malleable elongated shaft;
a housing at least partially circumscribing at least a portion of a proximal end of the elongated shaft and receiving or delineating at least a portion of the fluid supply conduit and a portion of the fluid exhaust conduit;
a flow restricting element in fluid communication with the fluid exhaust conduit, the flow restricting element regulating the flow of fluid through at least a portion of the fluid exhaust conduit;
a distal ablation section including a closed distal end in fluid communication with the fluid supply conduit and the flow restricting element, and in selective fluid communication with the fluid exhaust conduit, the distal ablation section extending distally beyond the flexible insulted conduit; and
a boiler comprising one or more channels providing fluid communication between the fluid supply conduit and an interior of the distal ablation section, the boiler comprising a central bore creating a fluid seal with an interior of the fluid exhaust conduit;
wherein the flow restricting element comprises a valve extending into the boiler downstream from the distal ablation section, the valve comprising a valve plug configured to engage a valve seat and form a seal therebetween, the valve plug being spring-biased to engage the valve seat; and wherein at least a portion of the distal ablation section is circumscribed by the flexible insulated conduit.

30. The cryogenic probe of claim 29, wherein:

the flexible insulated conduit includes at least one of a foam spacer and a helical spacer.

31. The cryogenic probe of claim 30, wherein at least one of the foam spacer and the helical spacer terminates before reaching a distal end of the flexible insulated conduit.

32. The cryogenic probe of claim 29, wherein the flexible insulated conduit is necked down to have radial maximum dimension that increases from distal to proximal proximate a distal end of the flexible insulated conduit.

33. The cryogenic probe of claim 30, wherein the flexible insulated conduit includes a radial maximum dimension at its distal end that is less than a radial maximum dimension of at least one of the foam spacer and the helical spacer.

* * * * *